United States Patent
Talbot et al.

(10) Patent No.: US 12,290,313 B2
(45) Date of Patent: May 6, 2025

(54) DUAL-FUNCTION MEDICAL DEVICES WITH DIAGNOSTIC AND THERAPEUTIC TOOLS

(71) Applicant: Boston Scientific Scimed, Inc., Maple Grove, MN (US)

(72) Inventors: Brian M. Talbot, Southborough, MA (US); Kevin Walsh, Wellesley, MA (US); Jeremy DiTullio, North Grafton, MA (US); Austin G. Johnson, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 741 days.

(21) Appl. No.: 17/480,893

(22) Filed: Sep. 21, 2021

(65) Prior Publication Data
US 2022/0096156 A1    Mar. 31, 2022

Related U.S. Application Data

(60) Provisional application No. 63/084,302, filed on Sep. 28, 2020.

(51) Int. Cl.
*A61B 18/22* (2006.01)
*A61B 8/12* (2006.01)
*A61B 18/00* (2006.01)
*A61B 18/14* (2006.01)

(52) U.S. Cl.
CPC ............ *A61B 18/22* (2013.01); *A61B 8/12* (2013.01); *A61B 18/14* (2013.01);
(Continued)

(58) Field of Classification Search
CPC .......... A61B 8/12; A61B 18/14; A61B 18/22; A61B 2018/00184; A61B 2018/00577;
(Continued)

(56) References Cited

U.S. PATENT DOCUMENTS

| | | |
|---|---|---|
| 5,029,588 A | 7/1991 | Yock et al. |
| 5,435,805 A | 7/1995 | Edwards et al. |

(Continued)

FOREIGN PATENT DOCUMENTS

| | | |
|---|---|---|
| JP | H02232068 A | 9/1990 |
| JP | 2000342703 A | 12/2000 |

(Continued)

OTHER PUBLICATIONS

Cherrington et al; "Hydrothermal Duodenal Mucosal Resurfacing: Role in the Treatment of Metabolic Disease," Gastrointestinal Endoscopy Clinics of North America, vol. 27, 2, pp. 299-311. 2017.

(Continued)

*Primary Examiner* — Chao Sheng
(74) *Attorney, Agent, or Firm* — Seager, Tufte & Wickhem, LLP

(57) ABSTRACT

The present disclosure relates generally to dual-function medical devices with diagnostic and therapeutic capabilities, such as real-time visualization and ablation. Many embodiments may include an ergonomic handle and dual-lumen catheter configured for dual-function diagnostic and therapeutic use during a medical procedure, such as a duodenoscope. The medical device may be delivered within an endoscope working channel to provide real-time visualization (e.g., radial ultrasound imaging) and treatment (e.g., soft tissue ablation) of cancerous tissue. For instance, a first lumen may include a high-frequency linear or radial ultrasound and the second lumen may include a surgical instrument, such as an ablation tool. Some embodiments may include a controller with a feedback loop configured to adjust the therapeutic tool based on data from the diagnostic tool. For instance, the power of an ablation tool may be adjusted by the controller based on data generated by an imaging device.

11 Claims, 28 Drawing Sheets

(52) U.S. Cl.
CPC .............. *A61B 2018/00184* (2013.01); *A61B 2018/00577* (2013.01); *A61B 2018/00773* (2013.01); *A61B 2018/00982* (2013.01); *A61B 2018/2266* (2013.01); *A61B 2218/002* (2013.01)

(58) Field of Classification Search
CPC ........... A61B 2018/00773; A61B 2018/00982; A61B 2018/2266; A61B 2218/002
See application file for complete search history.

(56) References Cited

U.S. PATENT DOCUMENTS

| | | | | |
|---|---|---|---|---|
| 5,505,088 | A | * | 4/1996 | Chandraratna ........ A61B 8/445 73/623 |
| 5,672,171 | A | | 9/1997 | Andrus et al. |
| 6,039,693 | A | * | 3/2000 | Seward ................. A61B 8/483 600/467 |
| 6,102,886 | A | | 8/2000 | Lundquist et al. |
| 2001/0011161 | A1 | | 8/2001 | Edwards et al. |
| 2018/0242948 | A1 | * | 8/2018 | Fleury ................ A61B 10/0233 |
| 2019/0008490 | A1 | | 1/2019 | Greminger et al. |
| 2020/0359996 | A1 | | 11/2020 | Walsh et al. |

FOREIGN PATENT DOCUMENTS

| | | | |
|---|---|---|---|
| JP | 2001104315 | A * | 4/2001 |
| JP | 2002306487 | A | 10/2002 |

OTHER PUBLICATIONS

Hadefi et al; "Endoscopic Duodenal Mucosal Resurfacing for the Treatment of Type 2 Diabetes," Digestive Diseases, 36, pp. 322-324, 2018.

Li et al; "Effect of Internal Iliac Artery Chemotherapy after Transurethral Resection of Bladder Tumor for Muscle Invasive Bladder Cancer," Chinese Journal of Cancer Research, vol. 26, 5 pp. 558-563, 2014.

Rajagopalan et al; "Endoscopic Duodenal Mucosal Resurfacing for the Treatment of Type 2 Diabetes: 6 Month Interim Analysis from the First-in Human Proof-of-Concept Study," Diabetes Care 1, vol. 39 (12) pp. 2254-2261, Dec. 2016.

Van Baar et al; "Duodenal Mucosal Resurfacing: Multicenter Experience Implementing a Minimally Invasive Endoscopic Procedure for Treatment of Type 2 Diabetes Mellitus," Endoscopy International Open vol. 8, 11 pp. E1683-E1689, 2020.

International Search Report and Written Opinion for International Application No. PCT/US2021/051313, dated Jan. 11, 2022.

* cited by examiner

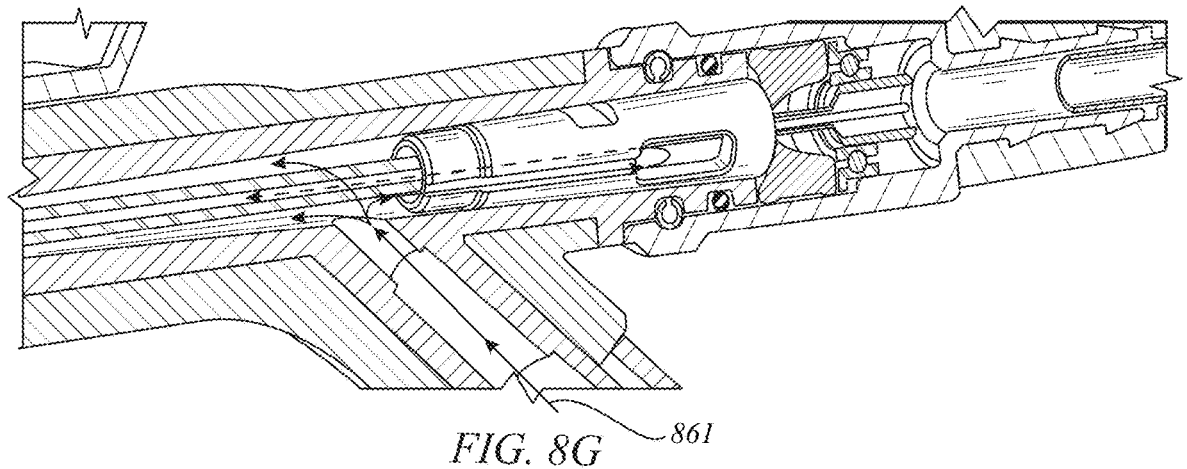
FIG. 8G  861
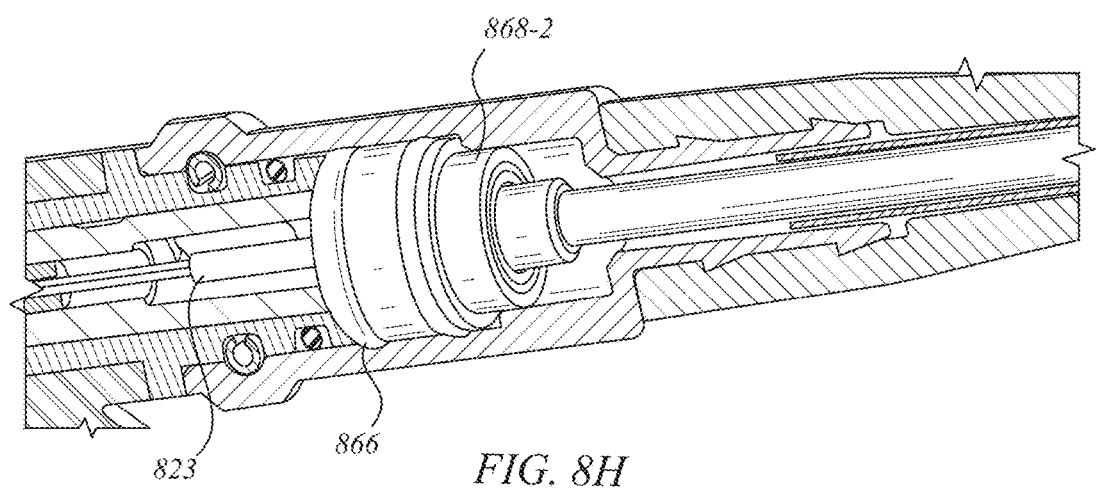
823  866  FIG. 8H

DUAL-FUNCTION MEDICAL DEVICES WITH DIAGNOSTIC AND THERAPEUTIC TOOLS

PRIORITY

The present application is a non-provisional of, and claims the benefit of priority under 35 U.S.C. § 119 to, U.S. Provisional Application Ser. No. 63/084,302, filed Sep. 28, 2020, the disclosure of which is incorporated herein by reference in its entirety.

FIELD

The present disclosure relates generally to the field of medical devices. In particular, the present disclosure relates to devices, systems and methods with diagnostic and therapeutic capabilities, such as imaging and ablation capabilities.

BACKGROUND

In medicine, diagnostic tools can be used to identify the nature or cause of a certain phenomenon and therapeutic tool can be used in an effort to remediate the certain phenomenon. For example, diagnostic tools may include imaging devices used to identify the nature of a cancerous tissue and therapeutic tools may include ablation tools used to ablate the cancerous tissue. Oftentimes, numerous diagnostic procedures must be performed before and/or after each therapeutic procedure. For example, a diagnostic tool (e.g., imaging) may be used to identify and locate a target anatomy, therapeutic tools (e.g., ablation) may be used to treat the target anatomy, and then another diagnostic tool (e.g., biopsy) may be used to verify the treatment.

It is with these considerations in mind that a variety of advantageous medical outcomes may be realized by the devices, systems and methods of the present disclosure.

SUMMARY

In one aspect, the present disclosure relates to an apparatus comprising a handle assembly, an elongate member, and a diagnostic tool. The handle assembly may include a bifurcation joint, flush port assembly, and a device port configured to receive a therapeutic tool. The elongate member may include a first lumen and a second lumen, wherein the bifurcation joint connects the flush port assembly to a proximal end of the first lumen and the device port to a proximal end of the second lumen. The diagnostic tool may extend though the flush port assembly, through the bifurcation joint, and into the first lumen.

In some embodiments, the apparatus includes the therapeutic tool, wherein the therapeutic tool extends through the device port, through the bifurcation joint, and into the second lumen. In various embodiments, the apparatus includes a probe with a first opening and a second opening, wherein the probe connects a distal end of the first lumen to the first opening and a distal end of the second lumen to the second opening. In various such embodiments, the first opening may be orthogonal to the second opening. In some such embodiments, the probe may include a ramped surface adjacent to the second opening, wherein the ramped surface is configured to deflect the therapeutic tool away from a longitudinal axis of the elongate member when the therapeutic tool is extended out of the second opening. In one or more such embodiments, the probe may include an imaging window and a marker. In many embodiments, the apparatus may include a plunger assembly configured to move the therapeutic tool in a distal and a proximal direction. In many such embodiments, the apparatus includes the therapeutic tool, wherein the therapeutic tool extends through the device port, through the plunger assembly, through the bifurcation joint, and into the second lumen. In several embodiments, the diagnostic tool includes an ultrasound transducer. In several such embodiments, the ultrasound transducer may operate at a frequency of more than 30 megahertz. In one or more embodiments, the flush port assembly is configured to rotate, at least partially, about a longitudinal axis of the diagnostic tool. In some embodiments, the first lumen has a diameter less than 0.75 millimeters. In various embodiments, the therapeutic tool includes an ablation tool. In many embodiments, the therapeutic tool includes one or more of a ball-tipped laser fiber and a blunt-ended radio frequency ablation tool. In several embodiments, the flush port assembly can rotate at least 180 degrees about the longitudinal axis of the diagnostic tool.

In another aspect, the present disclosure relates to a system, comprising an elongate member, a diagnostic tool, a therapeutic tool, and a controller. The elongate member may include a first lumen and a second lumen. The diagnostic tool may be disposed in the first lumen. The therapeutic tool may be disposed in the second lumen. The controller may be communicatively coupled to the diagnostic tool and the therapeutic tool. The controller may include a processor and memory, the memory having instructions that when executed by the processor cause the processor to generate an electromagnetic wave to operate the therapeutic tool and generate sensor data with the diagnostic tool.

In some embodiments, the memory includes instructions that when executed by the processor cause the processor to calibrate the electromagnetic wave based on the sensor data. In some such embodiments, the therapeutic tool comprises an ablation tool and calibration of the therapeutic tool comprises setting a power level of the ablation tool. In various embodiments, the sensor data comprises an ultrasound image. In many embodiments, the memory includes instructions that when executed by the processor cause the processor to identify ablated tissue based on the sensor data. In several embodiments, the memory includes instructions that when executed by the processor cause the processor to determine a depth of ablation based on the sensor data and set a power level of the therapeutic tool based on the depth of ablation.

In yet another aspect, the present disclosure relates to a method. The method may include one or more of imaging a target tissue with a diagnostic tool disposed within a first lumen of an elongate member; and treating the target tissue with a therapeutic tool disposed within a second lumen of the elongate member.

In some embodiments, the method includes imaging the target tissue with the diagnostic tool a second time after treatment of the target tissue with the therapeutic tool to verify treatment of the target tissue. In various embodiments, the method includes one or more of: scanning the target tissue with the therapeutic tool; imaging the target tissue scanned with the therapeutic tool; and setting a power level of the therapeutic tool based on imaging of the target tissue scanned with the therapeutic tool.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 8A-8J illustrate various aspects of an exemplary flush port assembly for a handle assembly according to one or more embodiments disclosed hereby.

DETAILED DESCRIPTION

Figure 1:
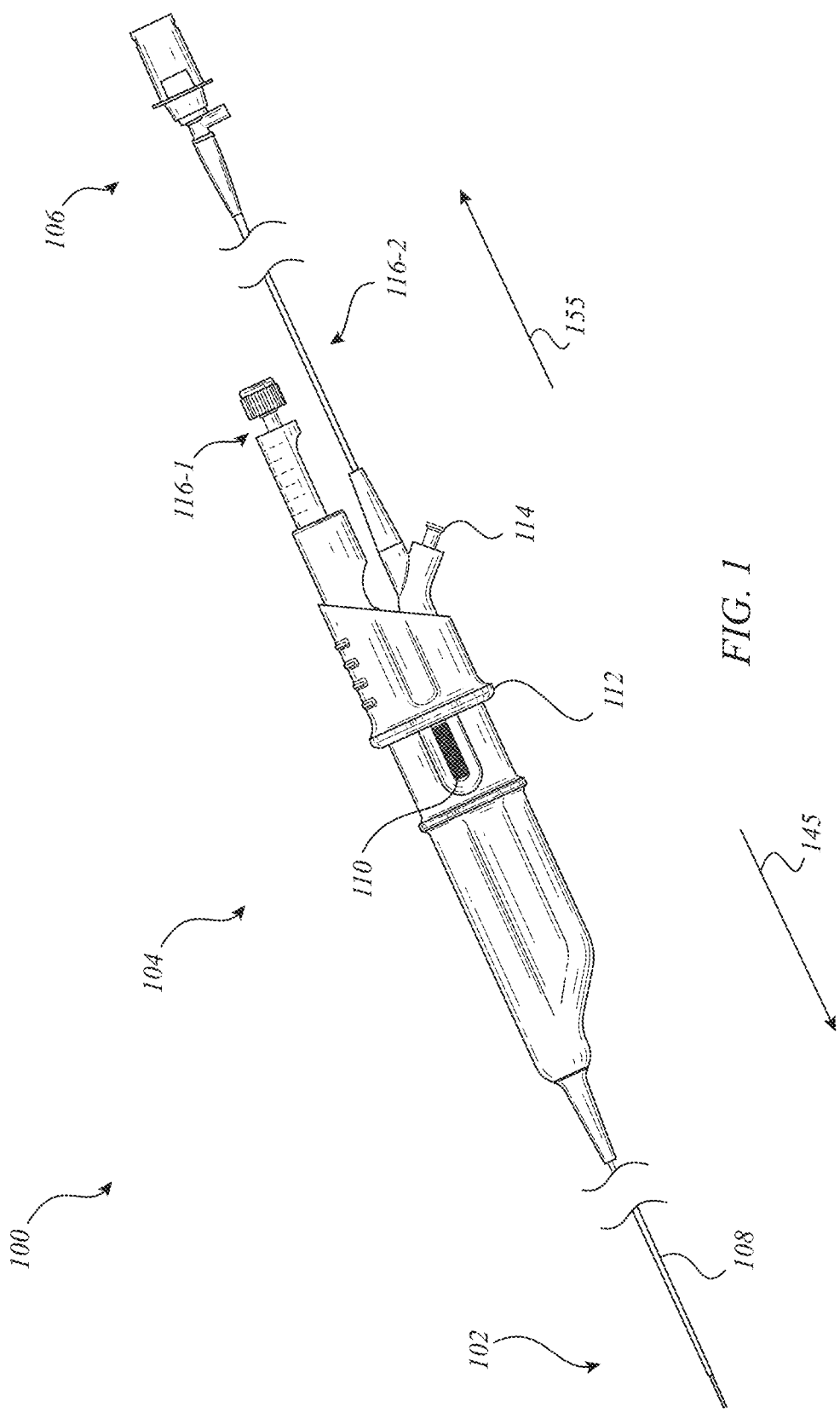
FIG. 1 illustrates an exemplary dual-function device according to one or more embodiments disclosed hereby.

The present disclosure relates generally to dual-function medical devices with diagnostic and therapeutic capabilities, such as real-time visualization and ablation. Many embodiments may include an ergonomic handle and dual-lumen catheter configured for dual-function diagnostic and therapeutic use during a medical procedure, such as a duodenoscope. The medical device may be delivered within an endoscope working channel to provide real-time visualization (e.g., radial ultrasound imaging) and treatment (e.g., soft tissue ablation) of cancerous tissue. For instance, a first lumen may include a high-frequency linear or radial ultrasound and the second lumen may include a surgical instrument, such as an ablation tool. Some embodiments may include a controller with a feedback loop configured to adjust the therapeutic tool based on data from the diagnostic tool. For instance, the power of an ablation tool may be adjusted by the controller based on data generated by an imaging device. Many embodiments disclosed hereby may allow a physician to endoscopically or laparoscopically treat a patient surgically before activating the diagnostic device (e.g., ultrasound imager) to scan the treatment area to ensure the procedure was completed as expected. This can remove the need to have pathology confirm the procedure was complete as expected, considerably improving efficiency, user experience, and patient experience. These and other embodiments are described and claimed.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Although endoscopes and endoscopic systems are referenced herein, reference to endoscopes, endoscopic systems, or endoscopy should not be construed as limiting the possible applications of the disclosed aspects. For example, the disclosed aspects may be used in conjunction with duodenoscopes, bronchoscopes, ureteroscopes, colonoscopes, catheters, diagnostic or therapeutic tools or devices, or other types of medical devices or systems.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates a dual-function device 100 according to one or more embodiments disclosed hereby. Generally, dual-function device 100 may include a probe 102, a handle assembly 104, and a hub assembly 106. The probe 102 may be connected to the handle assembly 104 via a dual-lumen catheter 108 that, among other features, facilitates the efficient and reliable use of a therapeutic tool 116-1 and a diagnostic tool 116-2. For example, the therapeutic tool 116-1 may include an ablation tool and the diagnostic tool 116-2 may include a radial ultrasound probe. The dual-function device 100 may include a distal end 145 at probe 102 and a proximal end at hub assembly 106. The handle assembly 104 may include a tool lock 110, an actuation member 112, and a flush port 114. The actuation member 112 may operate the therapeutic tool 116-1 between multiple positions when tool lock 110 is unlocked. In various embodiments, the therapeutic tool 116-1 may be extended out of the probe 102 during use and be retracted into the probe 102 when not in use. In various such embodiments, the therapeutic tool 116-1 may be lockable in each of the positions.

In one or more embodiments, the hub assembly 106 may interface with logic and/or control circuitry to operate at least the tool 116-2. For example, tool 116-2 may include one or more transducers for imaging that can be interfaced with a controller (e.g., imaging control 990 of FIG. 9) via hub assembly 106. In many embodiments, one or more components illustrated in FIG. 1, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

In various embodiments, the probe 102 may be inserted into a body lumen for diagnostic and/or therapeutic purposes. For example, dual-function device 100 may be utilized to image and/or ablate tissue within a patient. In some embodiments, the dual-function device 100 may be used as a stand-alone device for insertion into a body lumen. However, in additional, or alternative, embodiments the dual-function device 100 may be configured to extend through the working channel of another medical device (e.g., a duodenoscope, endoscope, ureteroscope, bronchoscope, colonoscope, arthroscope, cystoscope, hysteroscope, etc.). For instance, dual-function device 100 may be inserted via a duodeno scope for duodenal mucosal resurfacing.

In many embodiments, the dual-function device 100 may be modular (include one or more modular assemblies), such as to facilitate efficient manufacturing, selectable tools, and/or reliable operation. In several embodiments, the therapeutic and diagnostic tools 116-1, 116-2 may have a parallel configuration within the handle assembly 104. In several such embodiments, the parallel configuration may facilitate reliable and intuitive single-handed operation with either hand. For example, tool lock 110 may provide ambidextrous operation (see e.g., FIGS. 5C-5E). In some embodiments, one or more of the therapeutic and diagnostic tools 116 may be fixed, or removable, from within the probe and/or handle.

The flush port may facilitate fluid to be provided proximate the distal end 145, such as via the lumen of tool 116-2. In several embodiments, a fluid, such as saline, may be introduced via the flush port 114. In some embodiments, a fluid that assists with imaging may be introduced via the flush port 114, such as a conductive medium that displaces a another less conductive medium. For example, saline may be introduced to the distal end of medical device 100 via flush port 114 to enhance the propagation of sound waves from an ultrasound transducer, as tool 116-2 within probe 102, as compared to air. In some embodiments, flush port may be used to conduct other types of fluids for various other diagnostic or therapeutic purposes.

The dual-lumen catheter 108 and a proximal portion of tool 116-2 (e.g., between flush port 114 and hub assembly 106) may have the same, or different, diameters. In some embodiments, a common diameter may be enabled by the fact that the proximal portion of tool 116-2 has a larger diameter drive cable than the distal portion of tool 116-2 that extends through dual-lumen catheter 108. In many embodiments, the dual-lumen catheter 108 comprises an elongate member. In many embodiment, the elongate member (and/or the probe) may have an outside diameter between 1 and 10 millimeters. For example, the outside diameter may be 2 mm, 4.2 mm, or 7.3 mm. In some embodiments, the lumen for the diagnostic tool may have an inner diameter between 0.1 mm and 2 mm and the lumen for the therapeutic tool may have an inner diameter between 1 mm and 9.9 mm. For example, the lumen for the diagnostic tool may have a 0.71 inner diameter and the lumen for the therapeutic tool may have an inner diameter of 4 mm.

Figure 2A:
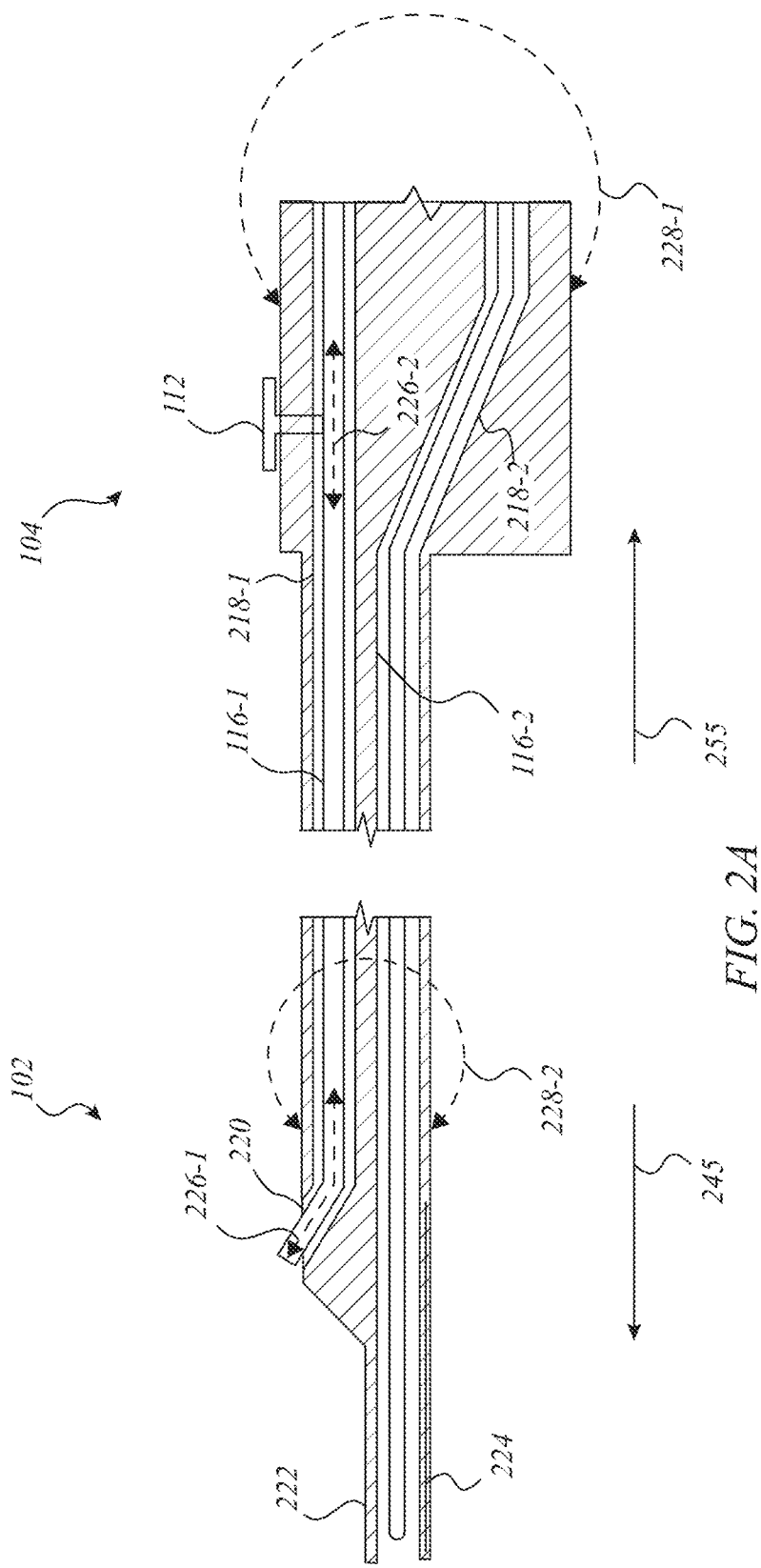
FIGS. 2A-2C illustrate various aspects of an exemplary dual-function device according to one or more embodiments disclosed hereby.
Figure 2B:
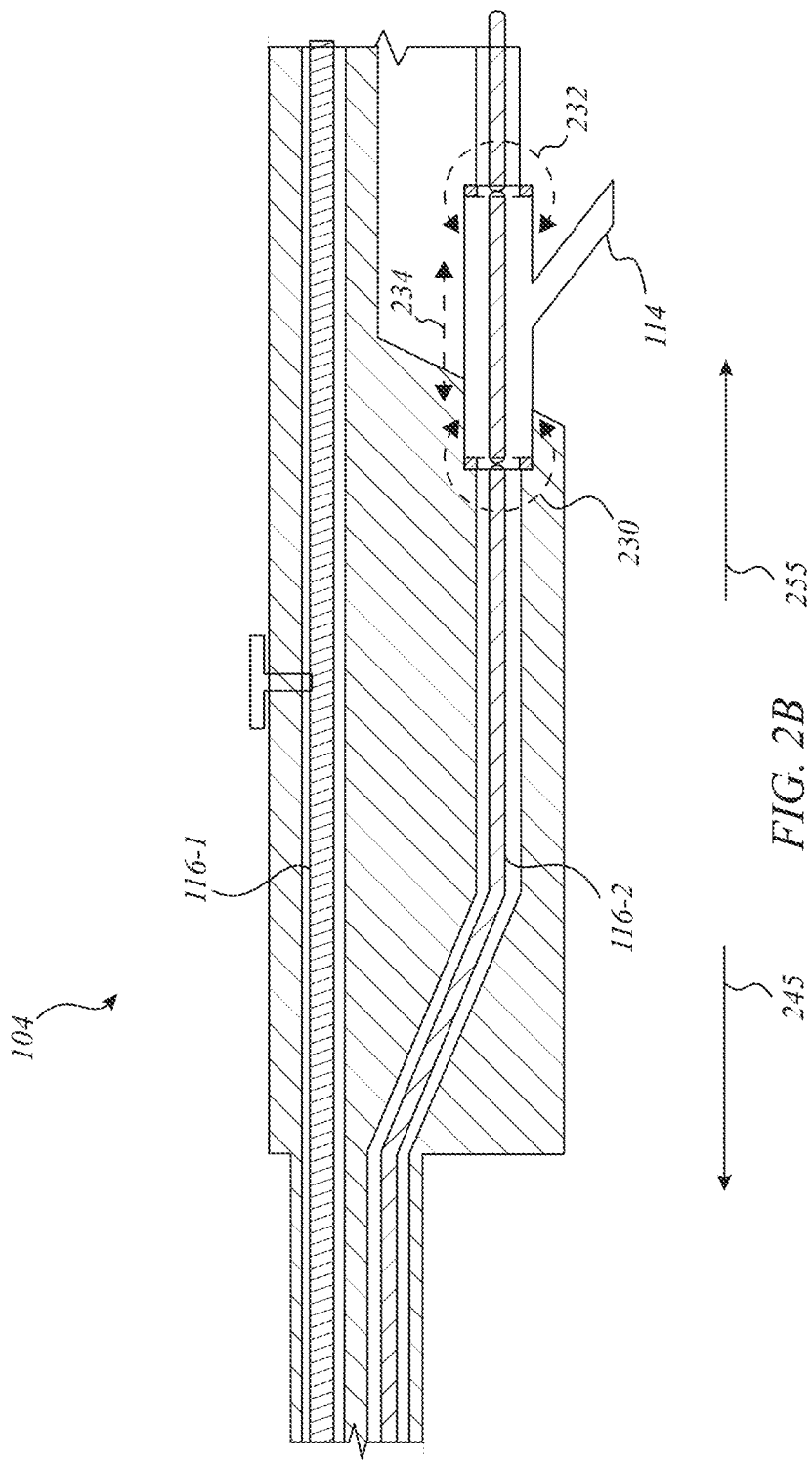
Figure 2C:
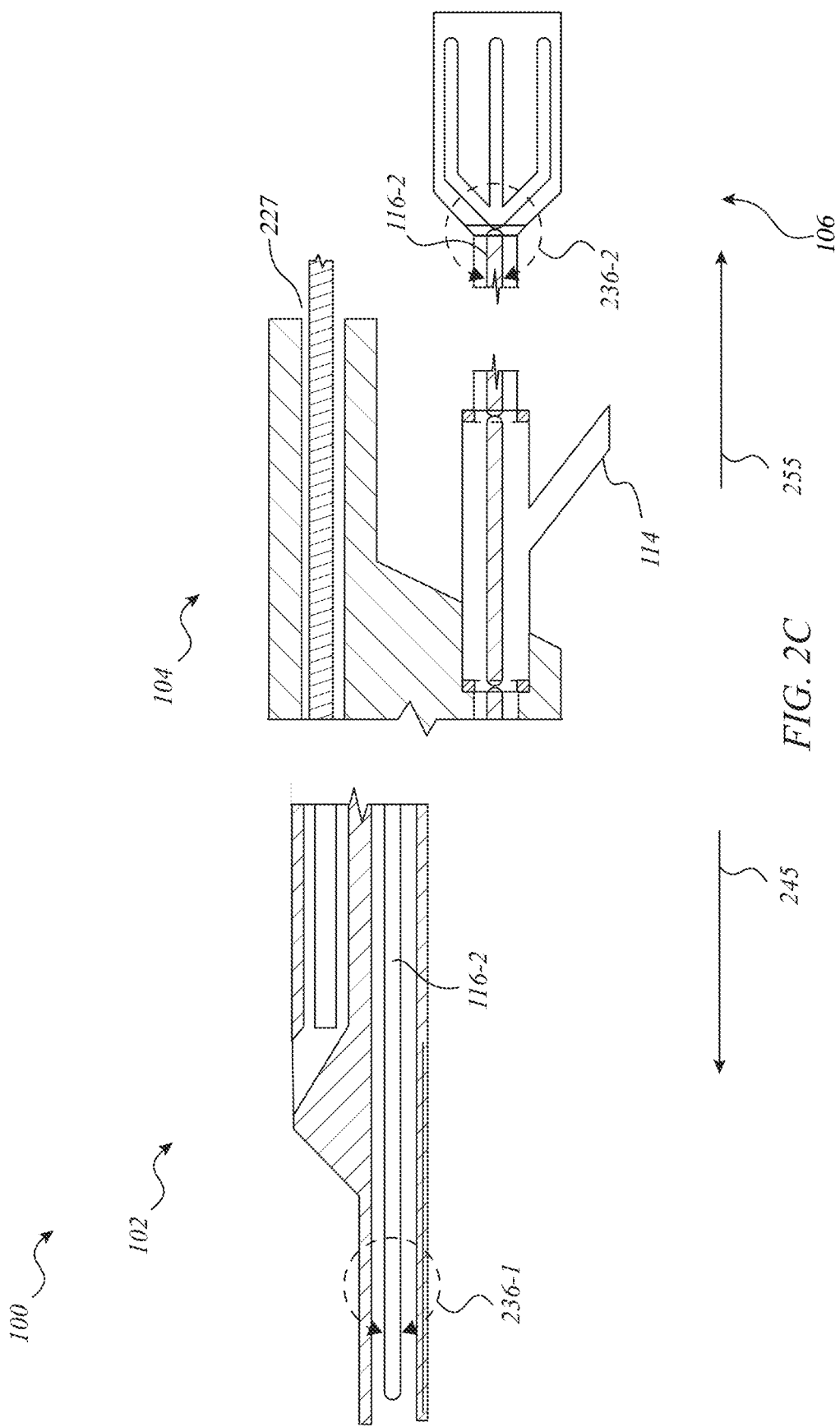

FIGS. 2A-2C illustrate various aspects of dual-function device 100 according to one or more embodiments disclosed hereby. More specifically, FIG. 2A illustrates axial displacements and rotations of one or more of probe 102, handle assembly 104, tool 116-1, and tool 116-2. FIG. 2B illustrates axial displacements and rotations between flush port 114 and handle body 243. FIG. 2C illustrates axial rotations of tool 116-2 between the distal and proximal ends 145, 155 of dual-function device 100. In embodiments disclosed hereby, components of the dual-function device 100 may rotate and/or translate in reliable, intuitive, and unique and advantageous ways. For example, embodiments many include an adjustable and leak-proof flush port assembly configured for use with a radial ultrasound system to provide real-time imaging and targeting of difficult to access treatment sites. For instance, the dual-function device 100 may extend beyond the distal end of a duodenoscope to access narrower gastrointestinal passages than the distal end of the duodenoscope can access. In such instances, e.g., the dual-function device may be configured to extend 15 centimeters or more beyond the distal end of the duodenoscope. Further, the adjustable flush port assembly may include an adjustable ultrasound probe and/or flush port configured to allow a physician to proximally/distally (e.g., along a longitudinal axis), laterally (e.g., along a radial axis), and/or axially (e.g., about or around a longitudinal axis) position/reposition components of the radial ultrasound system (e.g., ultrasound probe, flush port, and/or probe assembly) within a peripheral region of the body lumen while maintaining a leak-proof seal to simultaneously flush fluid through a lumen of the radial ultrasound probe. In many embodiments, one or more components illustrated in FIGS. 2A-2C, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

Referring to FIG. 2A, the probe 102 may include imaging window 222, side port 220, marker 224, and the handle assembly 104 may include actuation member 112. Additionally, lumens 218-1, 218-2 (or lumens 218) may extend approximately between the distal end 245 of probe 102 to the proximal end 255 of handle assembly 104. More specifically, the first lumen 218-1 may include a distal opening at side port 220 and the second lumen 218-2 may include a distal opening in or at the distal end 245. In some embodiments, one or more of the lumens 218 may be capped or sealed at the distal end. For example, lumen 218-2 may be capped by a balloon at the distal end 245. In various embodiments, the therapeutic tool 116-1 may be disposed in the first lumen 218-1 and the diagnostic tool 116-2 may be disposed in the second lumen 218-2. In one or more embodiments, the diagnostic tool 116-2 may include an imaging transducer, such as a high-frequency linear and/or radial ultrasound transducer. In one or more such embodiments, the therapeutic tool 116-1 may include an ablation tool, such as one or more of lasers, laser accessories, laser fibers, laser fiber accessories, ball-tipped laser fibers, and blunt-ended radio frequency ablation tools. In some embodiments a ball-tipped laser fiber and/or a blunt ended RF ablation tool may be used to prevent damage to/from a lumen (e.g., lumen 116-1 and/or a body lumen 990).

In the illustrated embodiment, the probe 102 includes an imaging window 222 and a marker 224. In many embodiments, imaging window 222 may refer to one or more portions of the probe 102 that are substantially transparent to the imaging energy wave lengths while marker 224 may refer to one or more portions of the probe that are relatively opaque to the imaging energy wave lengths. Marker 244 may comprise any medium that absorbs imaging energy wavelengths (e.g., ultrasound waves). For example, metal or metal alloys (e.g., stainless steel or nitinol) may be used. In some embodiments, non-metals may be used, such as air pockets embedded in the wall of the imaging window. In various embodiments, the marker 244 may be radiopaque, such as to show up on x-ray and/or fluoroscopic imaging additionally, or alternatively.

In such embodiments, marker 244 may be positioned to indicate in a generated image where the therapeutic tool 116-1 would be positioned when actuation member 112 is moved distally along axial displacement 226-2 to cause axial displacement 226-1 in tool 116-1, resulting in tool 116-1 extending out of side port 220. To position the probe 102 based on generated images, the handle assembly 104 may be rotated along axial rotation 228-1 to cause probe 102 to rotate along axial rotation 228-2. For example, the handle assembly 104 may be rotated to align the side port 220 with a target nodule based on indications of marker 224 in generated images. In some such examples, once aligned, actuation member 112 may be moved distally to cause the distal end of the therapeutic tool 116-1 to position proximate, or touching, the target treatment site. In various embodiments, a marker may be embedded in a wall of a lumen, such as the wall of the second lumen 218-2. As will be appreciated, device rotation (e.g., orientation of the marker and the therapeutic device radially) may enable more efficient ablation of tissue and/or eccentric nodules, e.g., when ablating target tissue that has irregular margins, is of an asymmetric shape, does not extend around an entire circumference of the body lumen, and the like, where control or orientation and position of the therapeutic device may be more critical.

As an example, marker 224 may be oriented around the circumference of the imaging window at a known angle from side port 220. In such a case, e.g., when targeting a treatment site for therapy, marker 224 may be oriented on the radial ultrasound image at the known angle from the intended treatment site, so that a therapeutic tool exiting side port 220 can be correctly aligned with the treatment site without blocking the view of the treatment site in the images. In a further such example, the marker 224 may be oriented on the radial ultrasound image 180 degrees across from the intended treatment site. In many embodiments, the known angle from the intended treatment site may be configured such that tolerances may be provided. For example, the marker 224 may be oriented on the radial ultrasound image 180±35 degrees from the intended treatment site.

Referring to FIG. 2B, the handle assembly 104 may have a distal end 245 and a proximal end 255 and include handle body 243 and flush port 114. In many embodiments, flush port 114 may have one or more of distal axial rotation 230, proximal axial rotation 232, and proximal/distal displacement 234. In several embodiments, the flush port 114 may rotate approximately 270 degrees without contacting with the plunger assembly and/or handle body. In many embodiments, rotation of the flush port 114 may allow the flush port 114 to be positioned such that the proximal drive cable does not interfere with usage, contributing to ease of one-handed control. In various embodiments, absent any interference structures, the flush port 114 may rotate 360 degrees.

Referring to FIG. 2C, the diagnostic tool 116-2 may extend from the hub assembly 106 through the flush port 114 to the distal end 245 of probe 102. In various embodiments, axial rotation 236-2 via hub assembly 106 may cause axial rotation 236-1 in probe 102. In various such embodiments, axial rotation 236-1 may enable tool 116-2 to generate a three hundred and sixty degree image and/or may allow tool 116-2 to be oriented rotationally as desired to align side port 220 and tool 116-1 with an intended target site. As will be discussed in more detail below, such as with respect to FIG. 9, hub assembly 106 may connect to an imaging controller that is able to rotate the tool 116-2 via the hub assembly 106. The tool port 227 may facilitate insertion of the therapeutic tool 116-1 into the proximal end of the handle assembly 104. In one or more embodiments, the tool port 227 may be orthogonal to the flush port 114. In various embodiments, the tool port 227 may create a slidable seal with the exterior of the therapeutic tool 116-1.

Figure 3A:
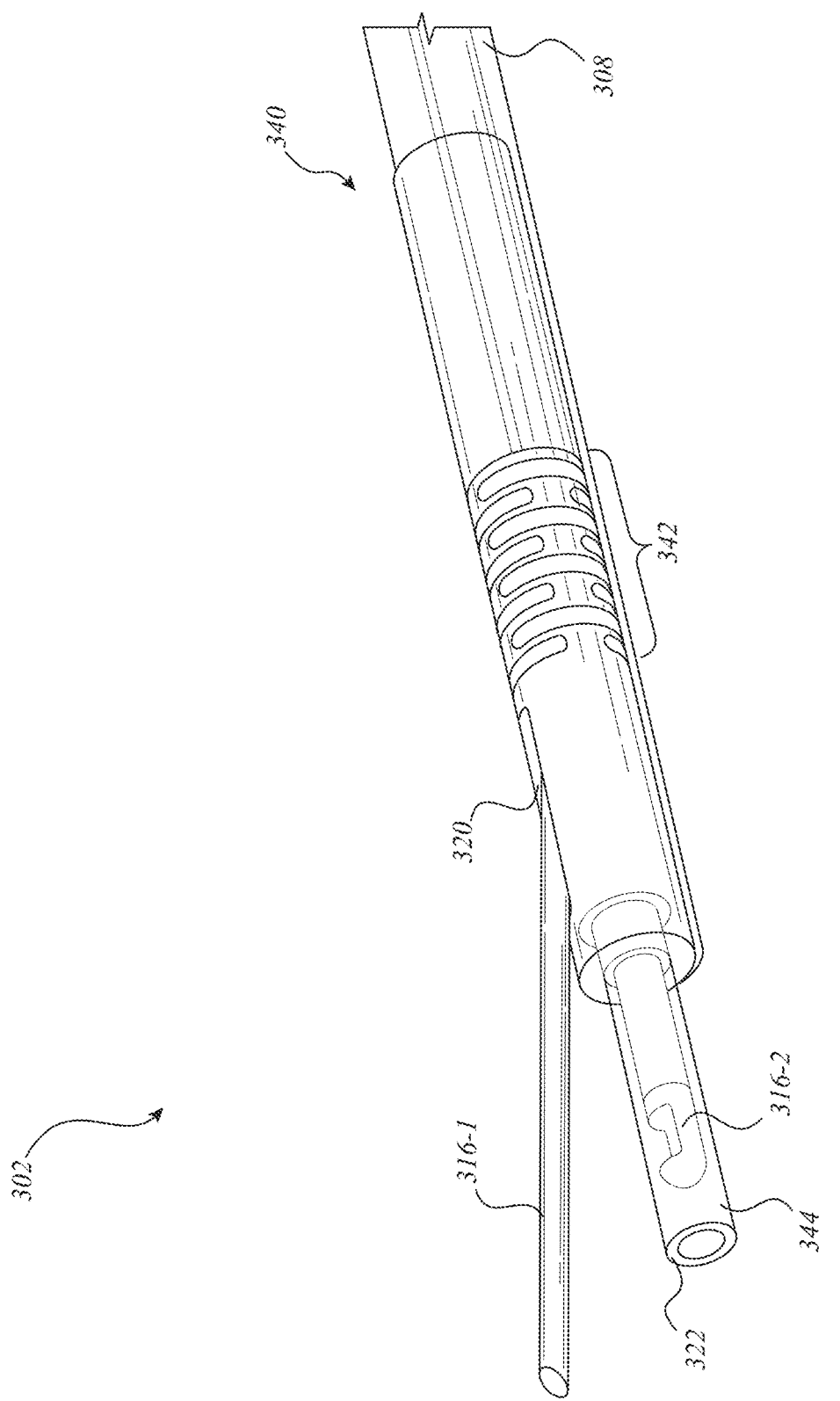
FIG. 3A-3H illustrate various aspects of an exemplary probe for a dual-function device according to one or more embodiments disclosed hereby.
Figures 3B, 3C:
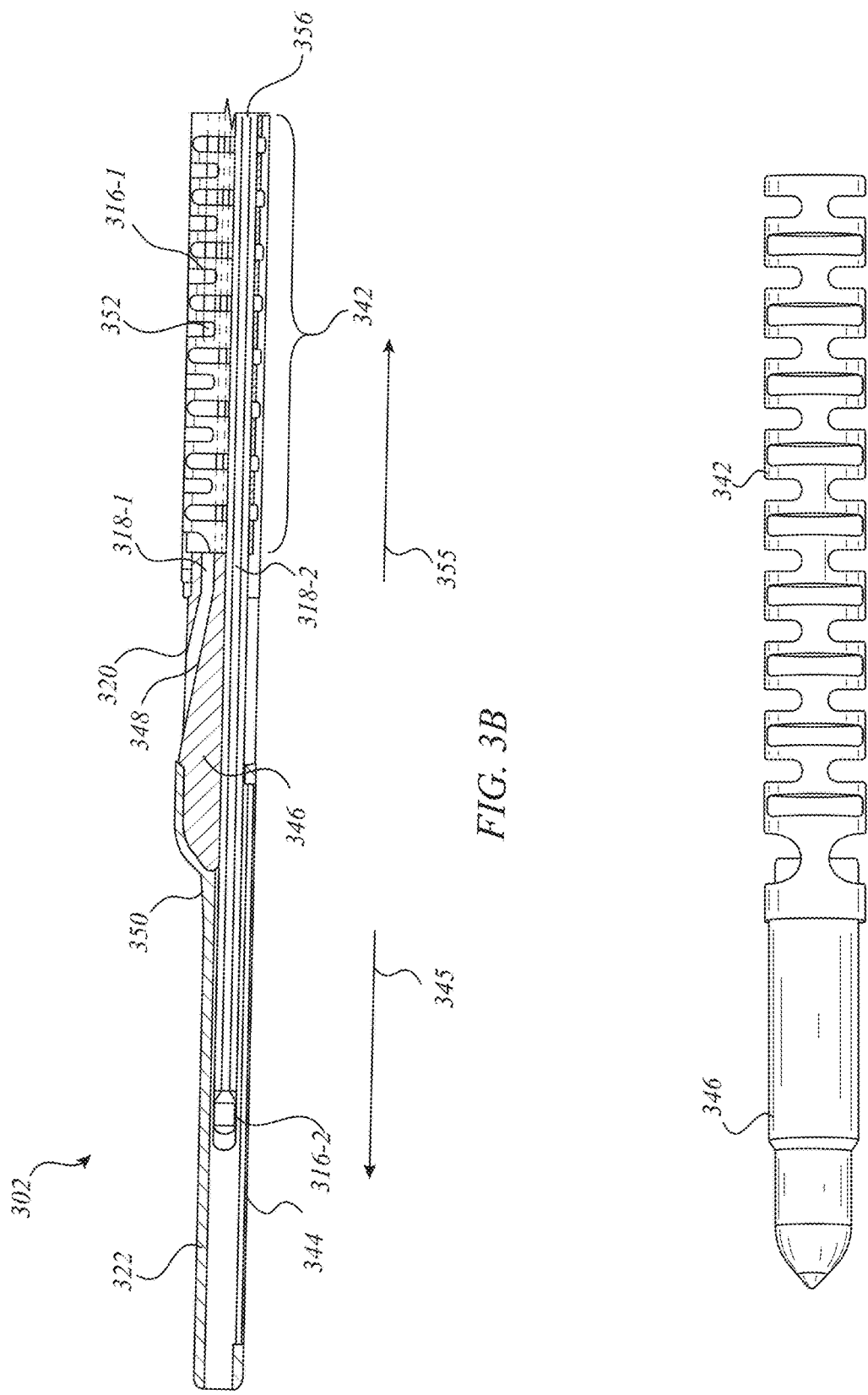
Figure 3D:
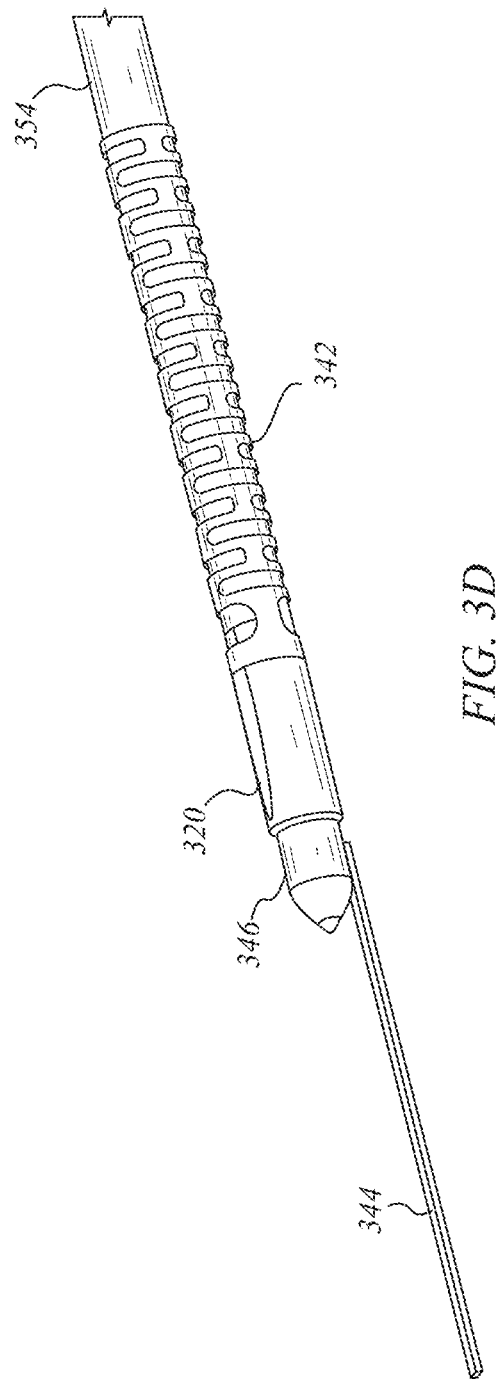
Figure 3E:
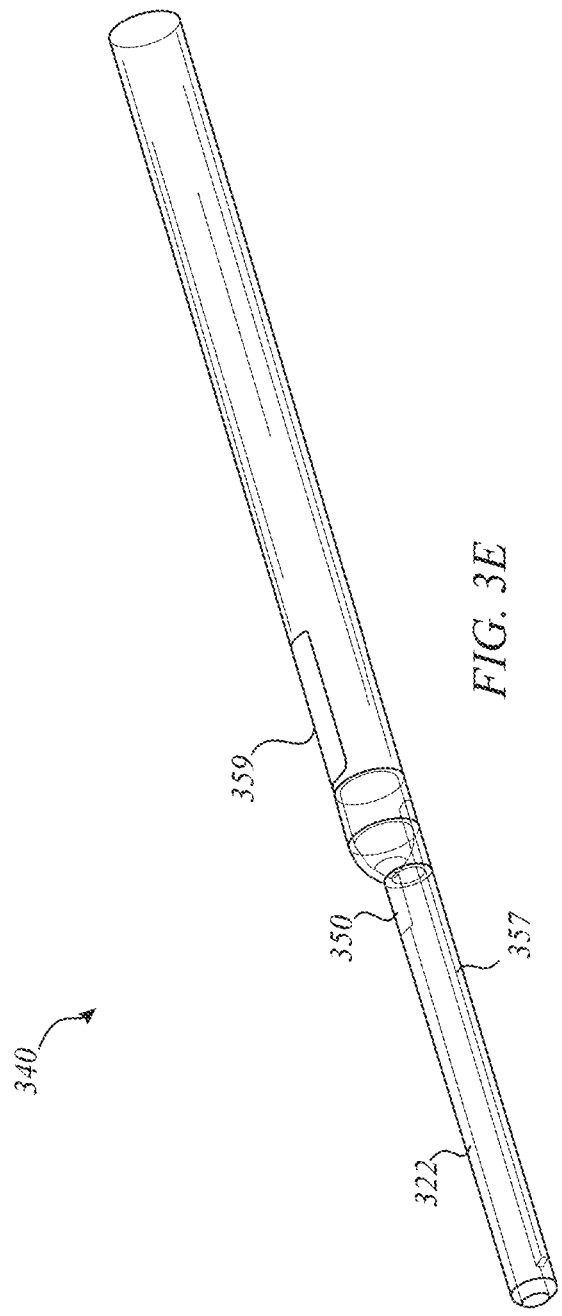
Figure 3F:
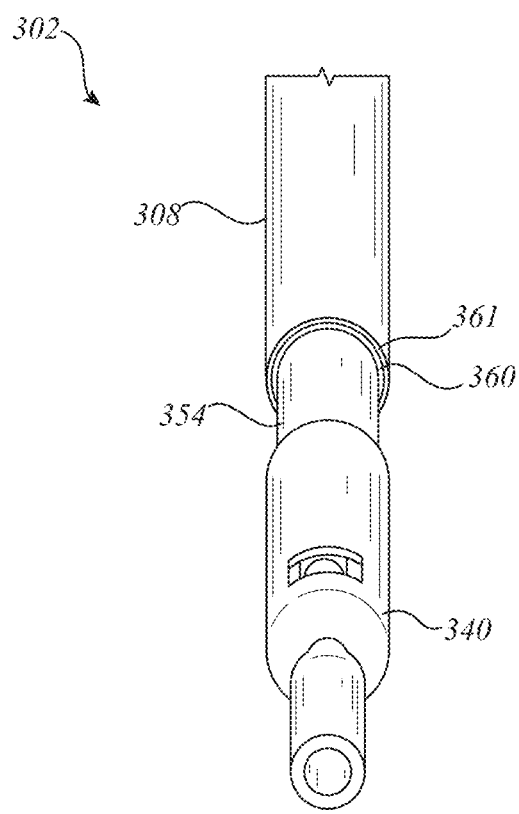
Figure 3G:
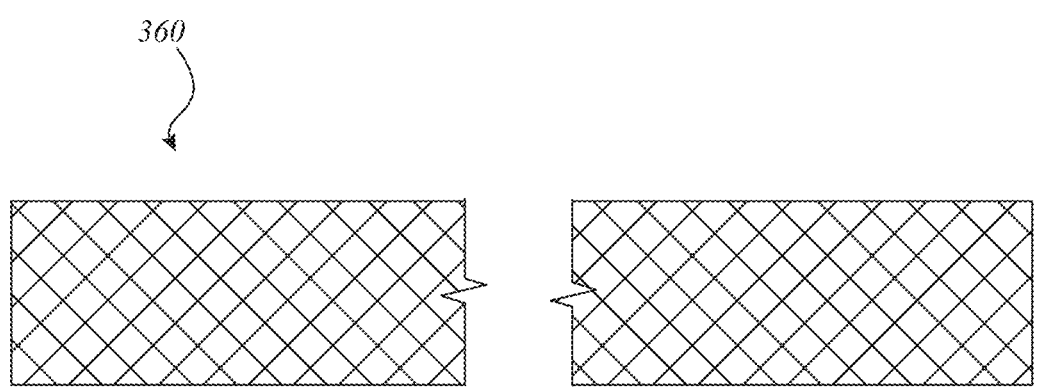
Figure 3H:
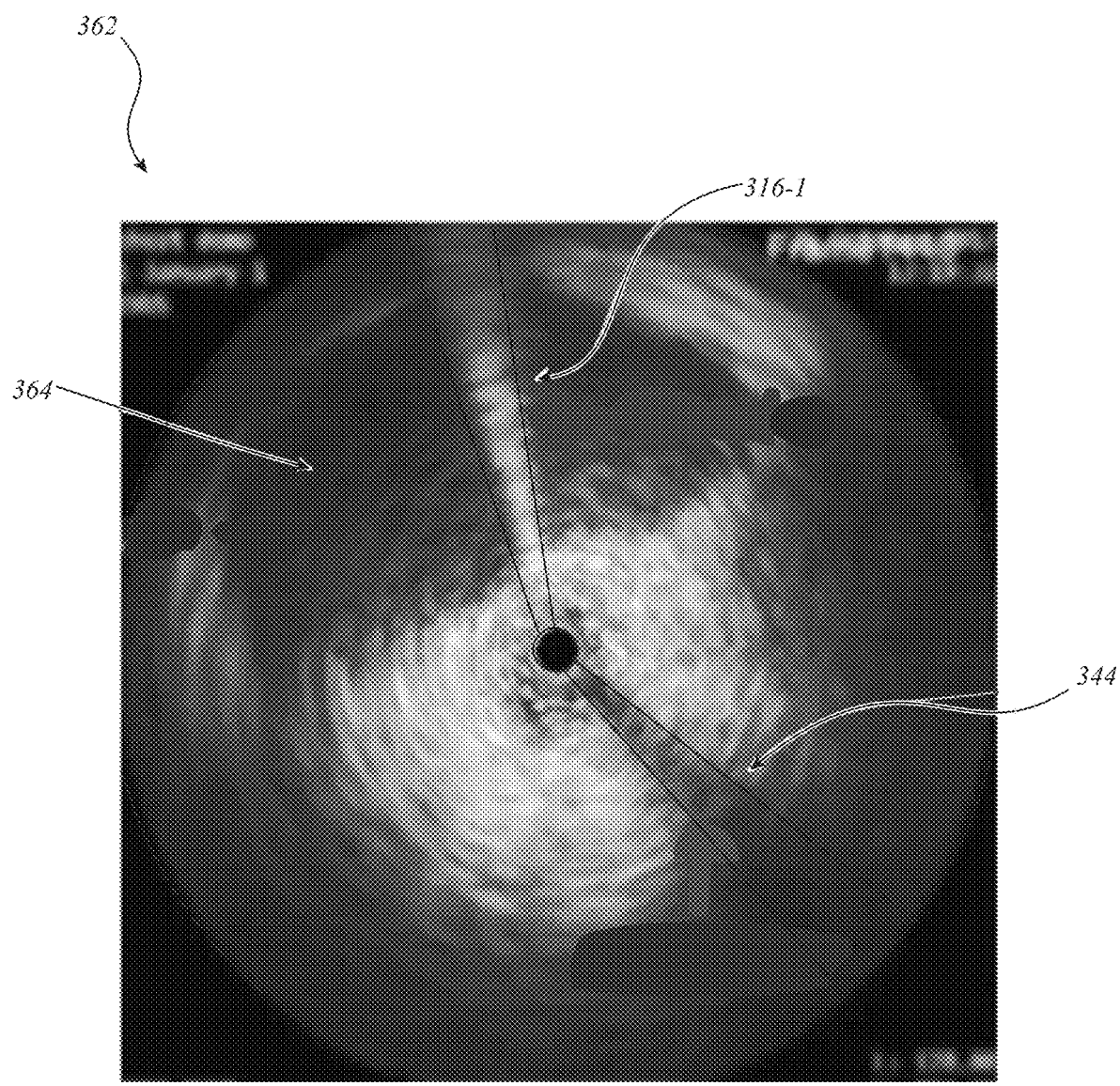

FIGS. 3A-3H illustrate various aspects of an exemplary probe 302 for a dual-function device according to one or more embodiments disclosed hereby. More specifically, FIG. 3A illustrates a perspective view of a probe 302 and FIG. 3B illustrates a cross-sectional view of the probe 302. FIG. 3C illustrates a collar 342 in conjunction with a distal juncture 346 of the probe 302. FIG. 3D illustrates the collar 342 and distal juncture 346 in conjunction with marker 344 and tubular member 354. FIG. 3E illustrates an endcap 340 of the probe 302. FIG. 3F illustrates a front perspective view of probe 302. FIG. 3G illustrates a braid 360 utilized in the dual-lumen catheter 308. FIG. 3H illustrates an example image 362 generated by the probe 302 (see e.g., FIG. 9). In embodiments disclosed hereby, components of the probe 302 may facilitate specific tissues to be targeted in reliable, intuitive, and unique and advantageous ways. For example, embodiments many include an endcap 340 disposed on the distal end of the dual-lumen catheter 308. Further, the endcap 340 may align with each lumen in catheter 308, enabling therapeutic device 316-1 to exit side port 320 and ultrasound transducer 316-2 to utilize imaging window 322 and marker 344. In many embodiments, marker 344 may provide indications and/or projections of the position of therapeutic device 316-1 as it exits side port 320. This, among other features, can provide techniques to improve the efficiency, accuracy, and/or reliability with which therapies, such as ablation, can be performed. For instance, the real-time images with marker 344 may allow a user to determine where and from what angle the ablation tool will exit the side port radially and/or ablate the tissue, prior to activation. Further, the effects of the therapeutic tool may be verified in real-time with the diagnostic device. As will be described in more detail below, such as with respect to FIG. 9, in many embodiments, a controller may automate one or more processes by implementing one or more control loops for the therapeutic device based on data from the diagnostic device. Embodiments are not limited in this context, and one or more aspects and/or components may be incorporated into other embodiments disclosed hereby without departing from the scope of this disclosure.

Referring to FIG. 3A, probe 302 may include endcap 340 coupled to dual-lumen catheter 308 (e.g., via overmolding and/or bonding by reflowing), ablation tool 316-1 extending out of side port 320, imaging window 322, marker 344, collar 342, and imaging transducer 316-2. As shown in the cross-sectional view in FIG. 3B, probe 302 may include first and second lumens 318-1, 318-2, ablation tool 316-1 with stylet 352 extending therethrough, imaging transducer 316-2 with distal cable 356, side port 320 with ramp 348, imaging window 322, collar 342, marker 344, distal juncture 346, and strain relief 350.

Referring to FIG. 3C, the distal juncture 346 may comprise a portion of the first and second lumens 318. The distal juncture 346 may include side port 320 and ramp 348. In various embodiments, the angle of the ramp 348 may be, with respect to the longitudinal axis in the proximal direction, between 0 and 90 degrees. In many embodiments, higher angles may improve nodule (e.g., an eccentric lesion) targeting, but make ablation tool actuation more difficult. For example, the higher the angle of the ramp 348, the larger the longitudinal force required to extend the ablation tool up the ramp 348 and out of the side port 320 to actuate the ablation tool. Further, higher angles may require the ablation tool to extend further out of the side port 320 to enter the field of view of the imaging transducer 316-2, limiting applicability to body lumens with larger diameters. Conversely, lower angles may require the probe 302 to be located closer to a target nodule, making it difficult to ablate target tissue. Accordingly, the ramp angle may be selected based on a particular application. In one or more embodiments, the ramp angle may be greater than or equal to 3 degrees and less than or equal to 20 degrees. For instance, the angle of ramp 348 may be 15 degrees. The distal juncture 346 and/or collar 342 may comprise a metal or metal alloy (e.g., nickel-titanium). In some embodiments, the collar 342 is laser cut. In many embodiments, the collar 342 may provide one or more of rigidity, confinement, structure, and flexibility. As shown in FIG. 3D, a tubular member 354 may extend into the collar 342. In various embodiments, tubular member 354 may comprise a portion of the dual-lumen catheter. Marker 344 is also illustrated in FIG. 3D. Marker 344 may comprise any medium that absorbs imaging energy wavelengths (e.g., ultrasound waves). For example, metal or metal alloys (e.g., stainless steel or nitinol) may be used. In some embodiments, non-metals may be used, such as air. For example, the marker 344 may comprise a pocket of air or a plurality of air bubbles extruded into the wall of the imaging window. In many embodiments, the angle of the ramp 348 may prevent interference between the therapeutic and diagnostic devices.

Referring to FIG. 3E, endcap 340 may receive the components illustrated in FIG. 3D. Marker 344 may be disposed in marker pocket 357 and side port 320 may be aligned with port window 359. In some embodiments, marker pocket 357 may comprise a pocket of air in a wall of endcap 340. Additionally, endcap 340 include imaging window 322 and strain relief 350. In one or more embodiments, imaging window 322 may be the same or similar material as the other portions of endcap 340. In various embodiments, the strain relief 350 may limit bending caused by marker 344 and/or distal juncture 346. In various embodiments, the gap between endcap 340 and the layers of braid 360 and reflow 361 remain to allow greater flexibility.

As illustrated in FIG. 3F, dual-lumen catheter 308 may include a tubular member 354 with two lumens, a layer of braid 360, and a layer of reflow 361 over the braid 360. As shown in FIG. 3G, the braid 360 may have an overlapping, woven, two wires per band, two over/two under and/or crisscross pattern. Other patterns, weave conditions, materials, and the like, may be contemplated based on a particular application of the dual-function device. In various embodiments, the number of crossovers per inch of braid 360 may be between 25 and 140. In some embodiments, different braid strands may be at between 60 and 120 degrees of each other, such as 90 degrees. In many embodiments, the pattern of braid 360 may be selected for a combination of flexibility and strength. In various embodiments, the braid 360 may be woven stainless steel or nitinol. In several embodiments, the braid 360 may provide torsional strength to the dual-lumen catheter. In several such embodiments, the torsional strength provided by the braid 360 may enable rotation of the handle to translate into rotation of the distal end. In many embodiments, rotation of the handle may result in rotation of the distal end (e.g., the probe) with a known ratio. For example, rotation of the handle may result in 1:1, or substantially 1:1, rotation of the distal end. Further, the ability to rotate the handle and cause rotation at the distal end may facilitate targeting of nodules, such as eccentric nodules, based on real-time images with marker indications. In many embodiments, endcap 340 may be coupled to the dual-lumen catheter 308 via a reflow and/or overmold process. In many embodiments, the dual-lumen catheter 308 may additionally, or alternatively, include a braided layer, such as braid 360. In some embodiments, the braid 360 may utilize up to 356 different strands. For example, some embodiments may utilize 64 different strands.

Figure 9:
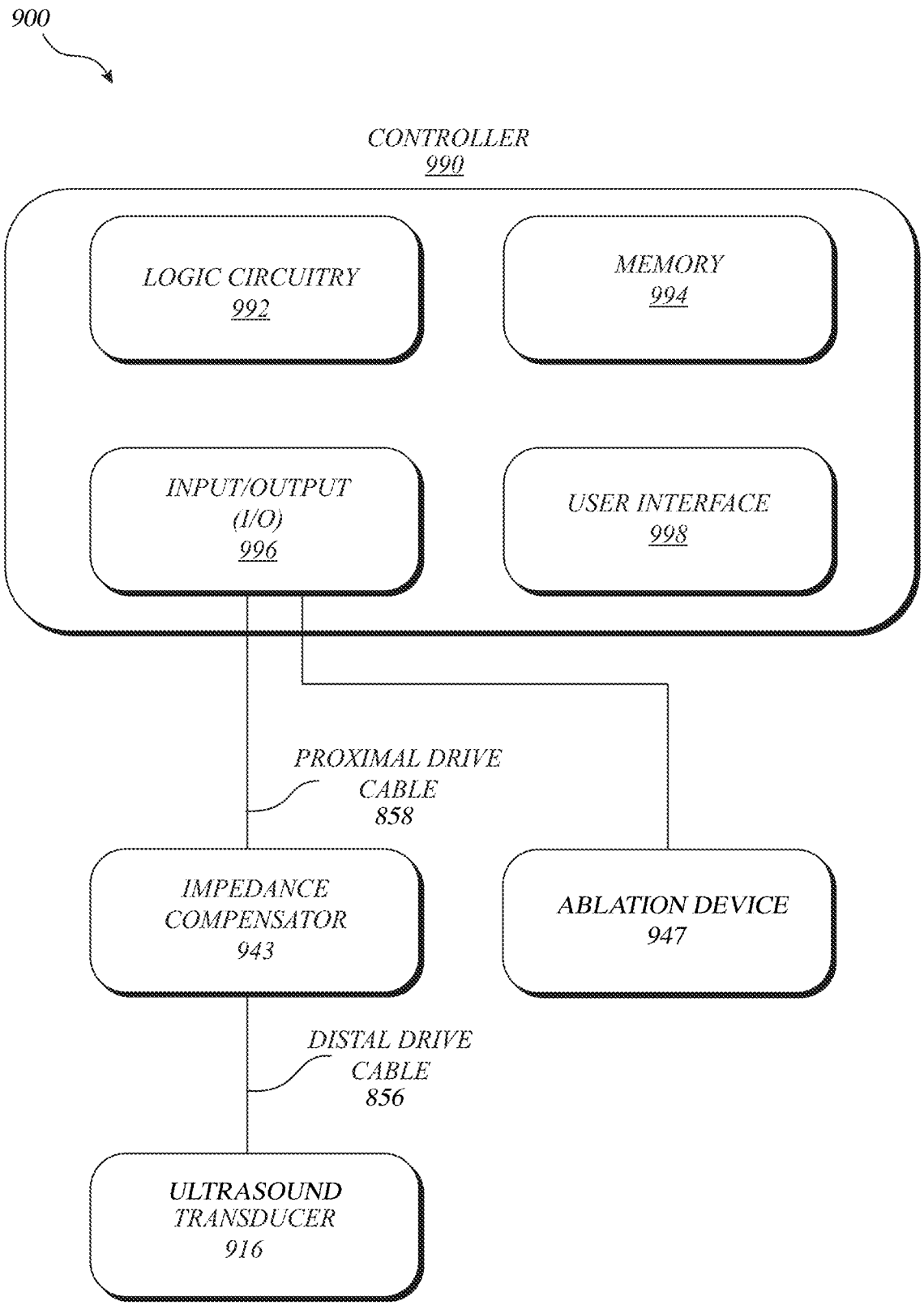
FIG. 9 illustrates various aspects of an exemplary controller according to one or more embodiments disclosed hereby.

FIG. 3H illustrates an example image 362 generated by the probe 302 (see e.g., FIG. 9). The image 362 may include marker 344, ablation tool 316-1, and nodule 364. As shown in FIG. 3H, marker 344 may provide indications and/or projections of the position of ablation tool 316-1 as it exits side port 320 in generated images (e.g., ultrasound images). This, among other features, can provide techniques to improve the efficiency, accuracy, and/or reliability with which treatment sites can be ablated. In the illustrated embodiment, ablation tool 316-1 is extended to demonstrate the indication it may provide on the image compared to marker 344.

In various embodiments, marker 344 may be oriented around the circumference of the imaging window at a known angle from side port 320. In such a case, e.g., when targeting nodule 364 (e.g., an eccentric or concentric tissue nodule) for ablation, marker 344 may be oriented on the image 362 (e.g., a radial ultrasound image) at the known angle from the intended treatment site, so that a ablation tool exiting side port 320 will be correctly aligned with the biopsy site. For example, in the illustrated embodiment, marker 344 may be oriented on the image 362 at 180±35 degrees from the intended treatment site (i.e., nodule 364).

Figure 4A:
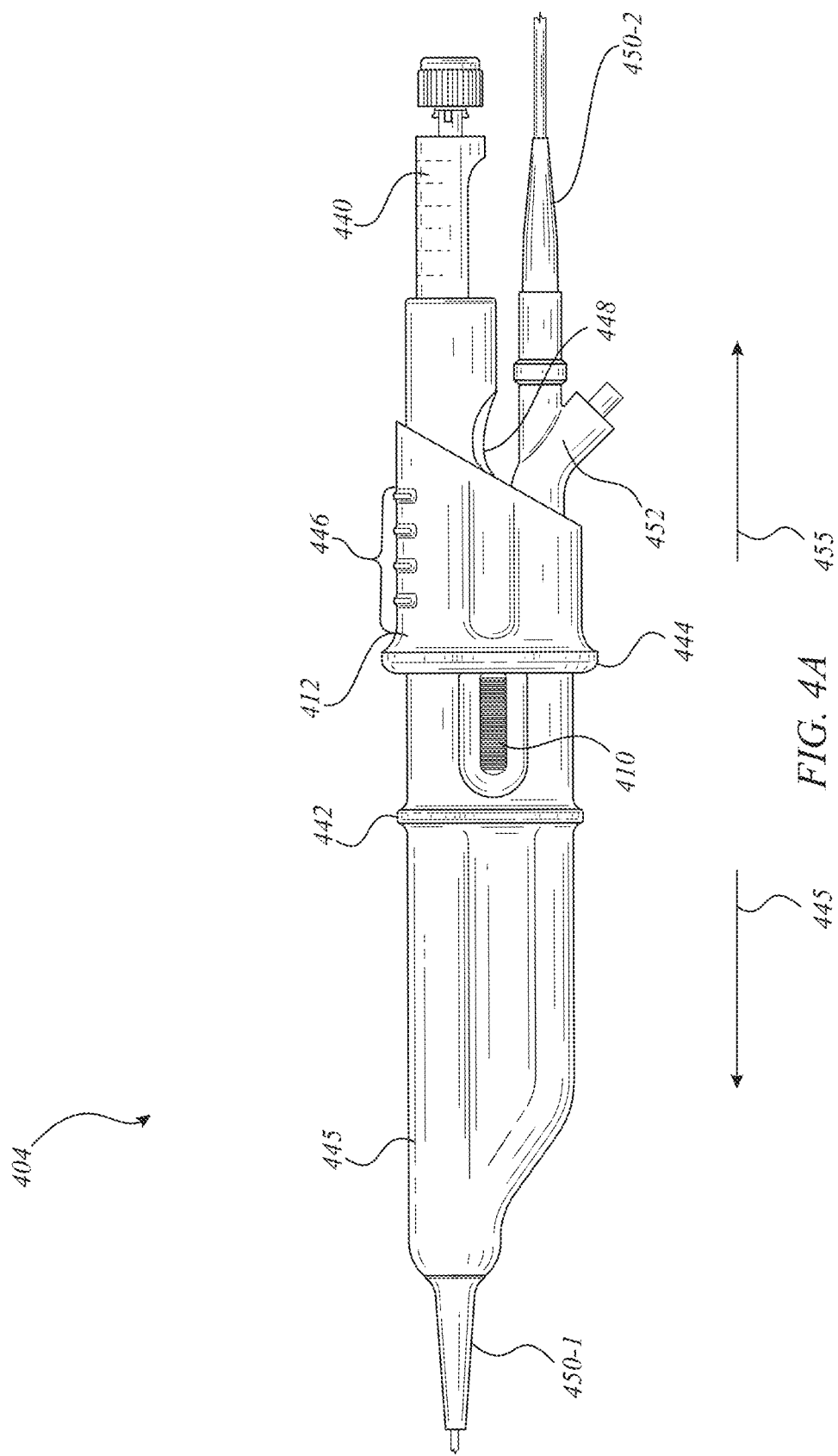
FIGS. 4A-4C illustrate an exemplary handle assembly for a dual-function device according to one or more embodiments disclosed hereby.
Figure 4B:
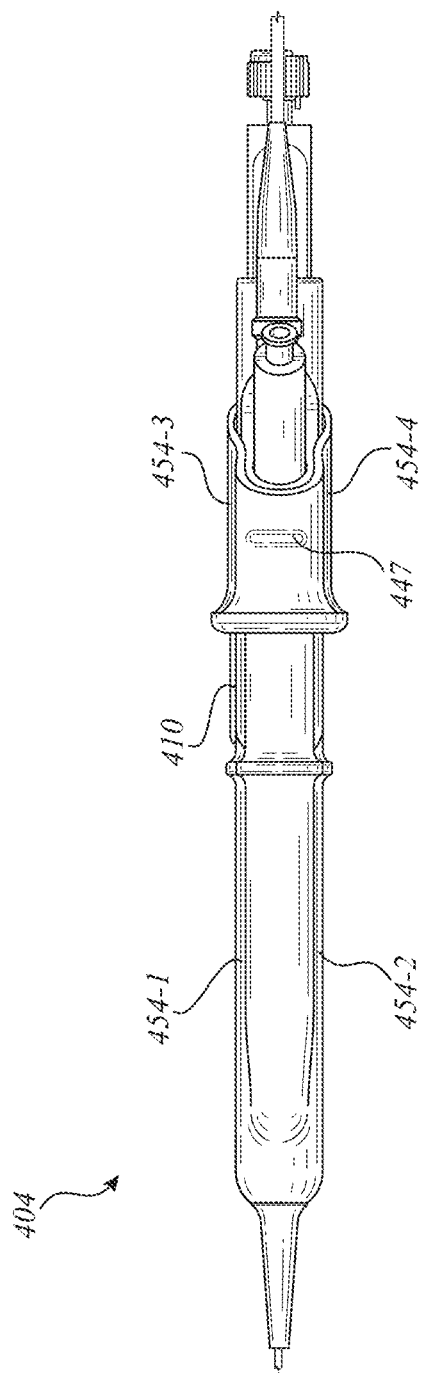
Figure 4C:
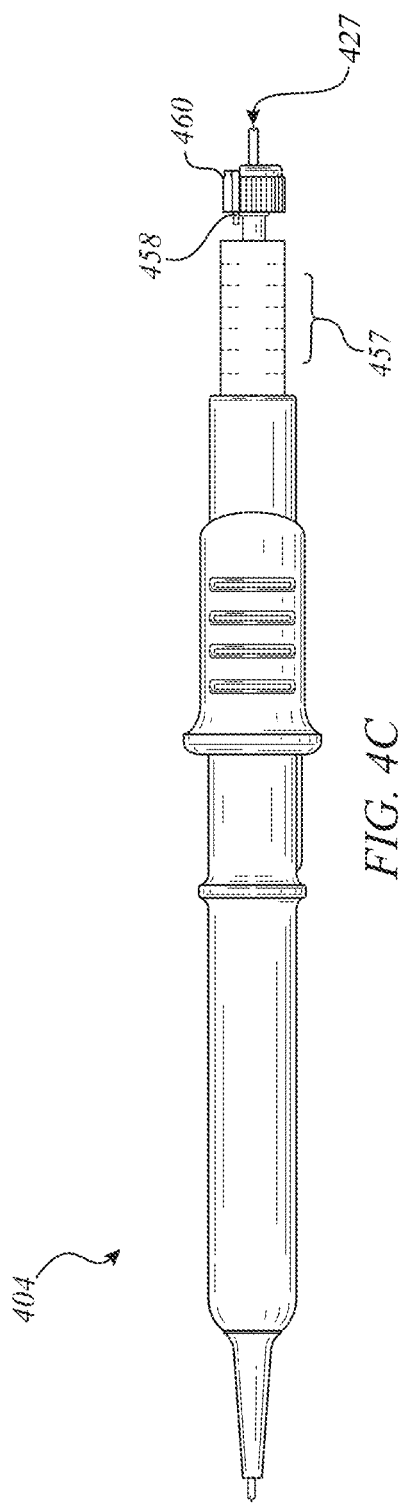

FIGS. 4A-4C illustrate an exemplary handle assembly 404 for a dual-function device according to one or more embodiments disclosed hereby. More specifically, FIG. 4A illustrates a side view of the handle assembly 404, FIG. 4B illustrates a bottom view of the handle assembly 404, and FIG. 4C illustrates a top view of the handle assembly 404. In embodiments disclosed hereby, components of the handle assembly 404 may facilitate intuitive, ergonomic, and/or single-handed operations to target specific tissues in reliable, intuitive, and unique and advantageous ways. For example, handle assembly 404 may include one or more ergonomic contours, grip ribs, ergonomic reliefs, component positionings and/or configurations to provide convenient, comfortable, accurate, and fatigue minimizing operation. For example, tool lock 410 may provide ambidextrous operation and/or dual sided access for single-hand use (e.g., tool lock 410 is accessible by thumb while rotating the handle). In another example, grip ridge 444 and grip ribs 446, 447 may provide non slip surfaces on actuation member 412. In many embodiments, one or more components illustrated in FIGS. 4A-4C, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

Referring to FIG. 4A, handle assembly 404 may have distal and proximal ends 445, 455 and include handle body 443, actuation stop 442, actuation member 412 with grip ribs 446 and grip ridge 444, tool lock 410, ergonomic relief 448, strain reliefs 450-1, 450-2, plunger assembly 440, and flush port assembly 452. Referring to FIG. 4B, handle assembly 404 may include one or more ergonomic contours 454-1, 454-2, 454-3, 454-4, tool lock 410, and grip rib 447. Referring to FIG. 4C, handle assembly 404 may include displacement gauge 457, Luer lock 458, and cap 460. In some embodiments, cap 460 may be a stylet cap and/or Luer lock 458 may be a syringe connector. In various embodiments, one or more of the ergonomic contours 454, grip ribs 446, 447, ergonomic reliefs 448, and/or grip ridges 444 may be symmetrical, complementary, and/or mirrored. Further, one or more surfaces may include textures and/or coatings to promote or fight friction. In one or more embodiments, tool port 427 may receive the distal end of a therapeutic tool. In some embodiments, cap 460 may lock and/or seal the therapeutic tool in the tool port 427.

Various handle assembly embodiments disclosed hereby may include one or more of a modular assembly, a bifurcated junction, linear ablation tool orientation, a manual slider (e.g., actuation member 112), a therapeutic tool lock (e.g., tool lock 110), an integrated flush port (e.g., flush port assembly 452), a syringe attachment, and dual strain relief (e.g., strain reliefs 450-1, 450-2). The dual-function device may include two independent modules: the ablation tool module and the ultrasound module. These two modules may be assembled separately and joined together inside the handle body 443. In various embodiments, one or more of the modules may be interchangeable. For instance, the ablation module may be replaced with a module with a different tool, such as another diagnostic and/or therapeutic medical tool. The ablation line and the ultrasound line may converge inside a bifurcated junction (e.g., bifurcation junction 664) before feeding into a dual-lumen catheter. The bifurcated junction may dictate the bend radius of the ultrasound line. The ablation module (e.g., plunger assembly 640) may be axially aligned with a lumen (e.g., lumen 218-1), such as to reduce the force required to actuate the ablation tool. In other words, the ablation module may extend linearly into a first lumen of the dual-lumen catheter.

In various embodiments, one or more features of the dual-function device may provide for tactile registration. In some embodiments, the extended handle profile and short transition curve may provide more comfortable and substantial grip locations and/or accommodate a wider range of hand sizes. For example, handle assembly 404 may accommodate adult hand sizes ranging from the $5^{th}$ percentile of female hands to the $95^{th}$ percentile of male hands. The displacement gauge 457 (e.g., corresponding to graduated displacement distances of the ablation tool exiting the ramp and the side port) may be readily readable from a variety of viewing angles, such as by partially wrapping around the plunger. In some embodiments, a soft-touch finish on the actuation member 412 may create a contrasting feel to the handle body 443 and/or match the distal handle finish. Some components may include rubberized texture overmolds and/ or color accent, such as on the actuation member grip ridge 444. In some embodiments this and other features may provide an improved thumb grip and/or visual travel indication. The handle body may have a smooth/semi-gloss finish in some embodiments. Various embodiments may include a horizontal groove texture on the tool lock 410, such as for an ergonomic detail and/or precision feel. Several embodiments include a textured finish around the tool lock 410 to create tactile contrast, such as for intuitive use. The actuation stop 442 (or hand hilt) and/or grip ridge 444 may provide 360 degree tactile registration. In some embodiments, the actuation stop 442 and/or grip ridge 444 may provide a boundary for hand position and/or hand protection during actuation. Further, the actuation stop 442 and/or grip ridge 444 may provide a non-visual indicator of hand position. Various embodiments may include a soft touch finish and/or slight rubberized texture on a distal portion of the handle body 443.

Several embodiments may include a solid color band that wraps around the handle body to indicate ultrasound zone is exposed when the actuation member 412 is moved distally. In several such embodiments, the band may include a slight texture change and/or an ultrasound icon disposed proximately. In one or more embodiments, an additional part break line on a strain relief connection may allow for individual rotation.

Figure 5A:
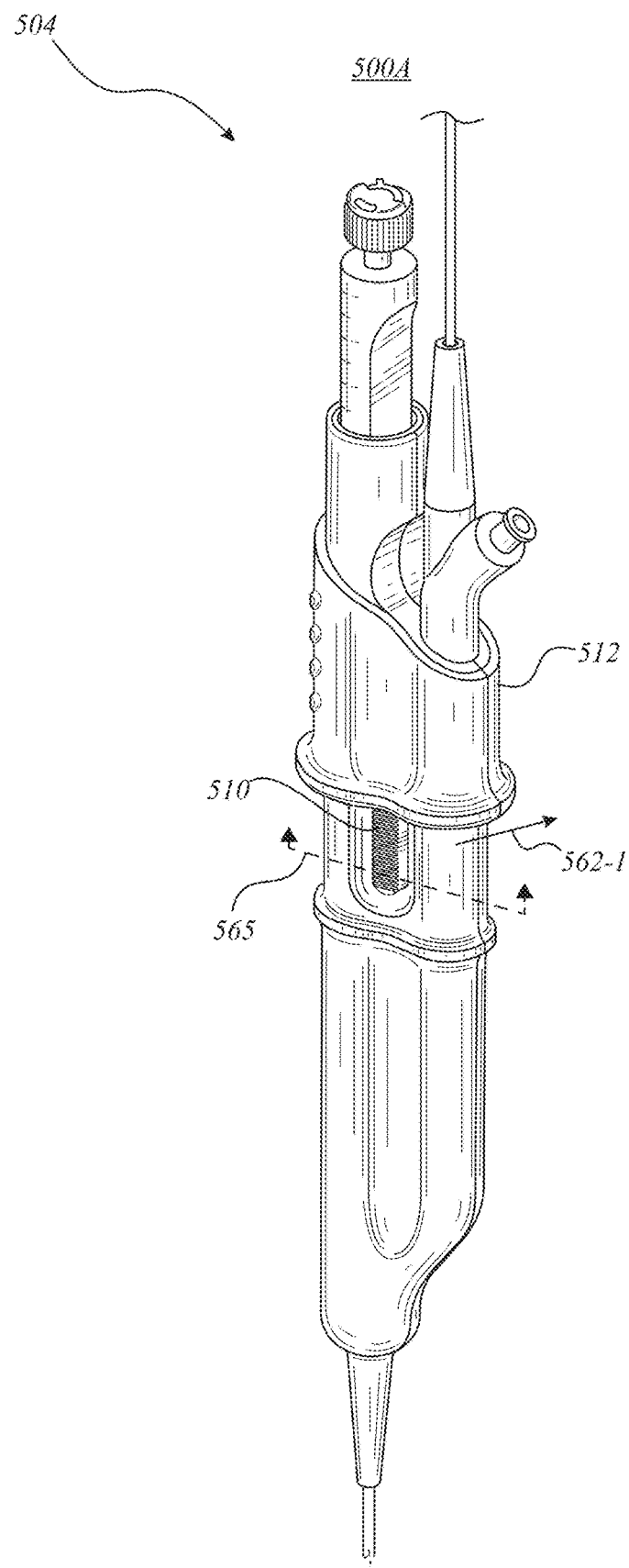
FIGS. 5A-5E illustrate various aspects of an exemplary handle assembly according to one or more embodiments disclosed hereby.
Figure 5B:
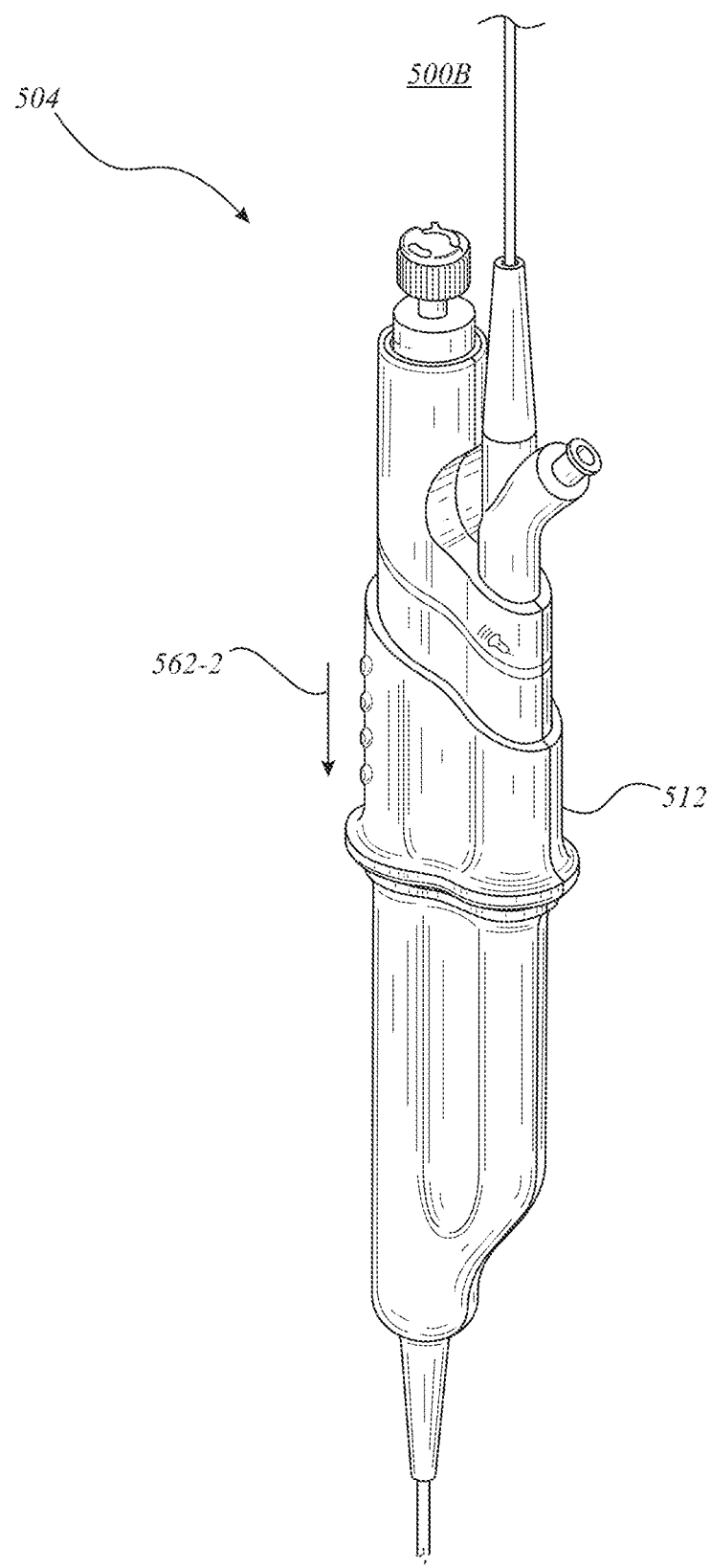
Figure 5C:
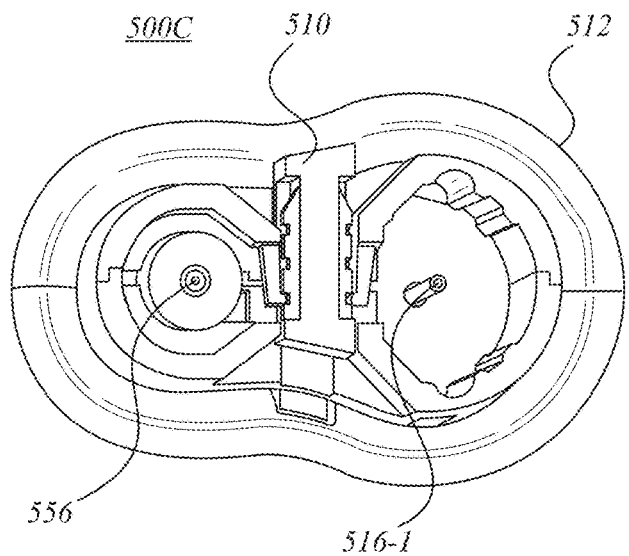
Figure 5D:
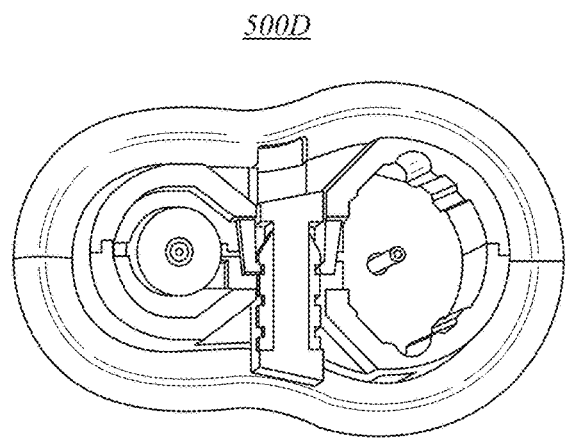
Figure 5E:
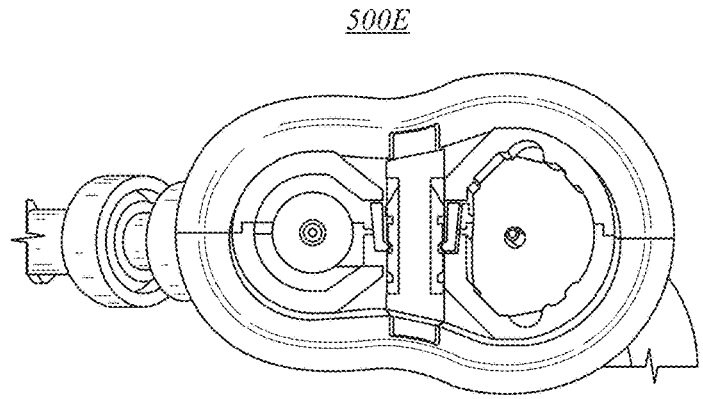

FIGS. 5A-5E illustrate various aspects of an exemplary handle assembly 504 for a dual-function device according to one or more embodiments disclosed hereby. More specifically, FIG. 5A illustrates the handle assembly 504 in an unactuated configuration 500A and FIG. 5B illustrates the handle assembly 504 in an actuated configuration 500B. In various embodiments, actuation member 512 may be moved distally to cause a tool, such as an ablation tool, to exit the side port of the probe as indicated in the image by the marker. FIGS. 5C-5E illustrate operation of a tool lock 510 of handle assembly 504. In embodiments disclosed hereby, components of the handle assembly 504 may facilitate intuitive, ergonomic, and/or single-handed operations to target specific tissues in reliable, intuitive, and unique and advantageous ways. For example, handle assembly 504 may utilize intuitive motions for gripping, locking, unlocking, and actuating to provide for convenient, comfortable, accurate, and fatigue minimizing operation. In many embodiments, one or more components illustrated in FIGS. 5A-5E, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

Referring to FIG. 5A, the handle assembly 504 is in unactuated configuration 500A when the distal end of actuation member 512 is positioned proximal of the tool lock 510. In the unactuated configuration 500A, tool lock can be engaged or disengaged. An unlock movement 562-1 may be used to position the tool lock 510 in the middle such that actuation member can move distally over either side of the tool lock 510 in an actuation movement 562-2 to place the handle assembly 504 in an actuated configuration 500B (see e.g., FIG. 5B). The positioning of the tool lock will be discussed in more detail below with reference to cross-sectional line 565. In many embodiments, tool lock 510 may provide a visual indicator of the lock status of the plunger assembly. The ultrasound flush port valve (e.g., flush port assembly) may be integrated into the handle assembly and/or handle body design. In several embodiments, the flush port is positioned and/or positionable away from a grip zone of a user. In various embodiments, the dual-function device may utilize syringes (e.g., for ultrasound flushing). In many embodiments, syringes may attach to the dual-function device with stopcocks, Luer-lock fittings, and/or check valves. For example, a check valve may be positioned between the flush port and a syringe connector (e.g., Luer-lock). The handle assembly may include integrated strain relief at both the distal and proximal ends of the handle body (see e.g., strain reliefs 450-1, 450-2). In some embodiments, the distal strain relief (e.g., strain relief 450-1 may be utilized as an additional grip space).

Referring to FIGS. 5C-5E, handle assembly 504 may have positions 500C, 500D, 500E in addition to the unactuated configuration 500A and the actuated configuration 500B. In position 500C, the tool lock 510 may be in a first locked position with actuation member 512 being blocked from moving distally (out of the page). Similarly, in position 500D, the tool lock 510 may be in a second locked position with actuation member 512 being blocked from moving distally (out of the page). In position 500E, tool lock 510 may be in an unlocked position with actuation member 512 not blocked from moving distally (out of the page). This arrangement may allow for actuation of the tool lock 510 from either side of the handle, depending on which side is more accessible to the fingers of the user. Further, as the distal direction is out of the page in FIGS. 5C-5E, it will be appreciated that although the flush port would be visible, it is not illustrated for simplicity.

Figure 6A:
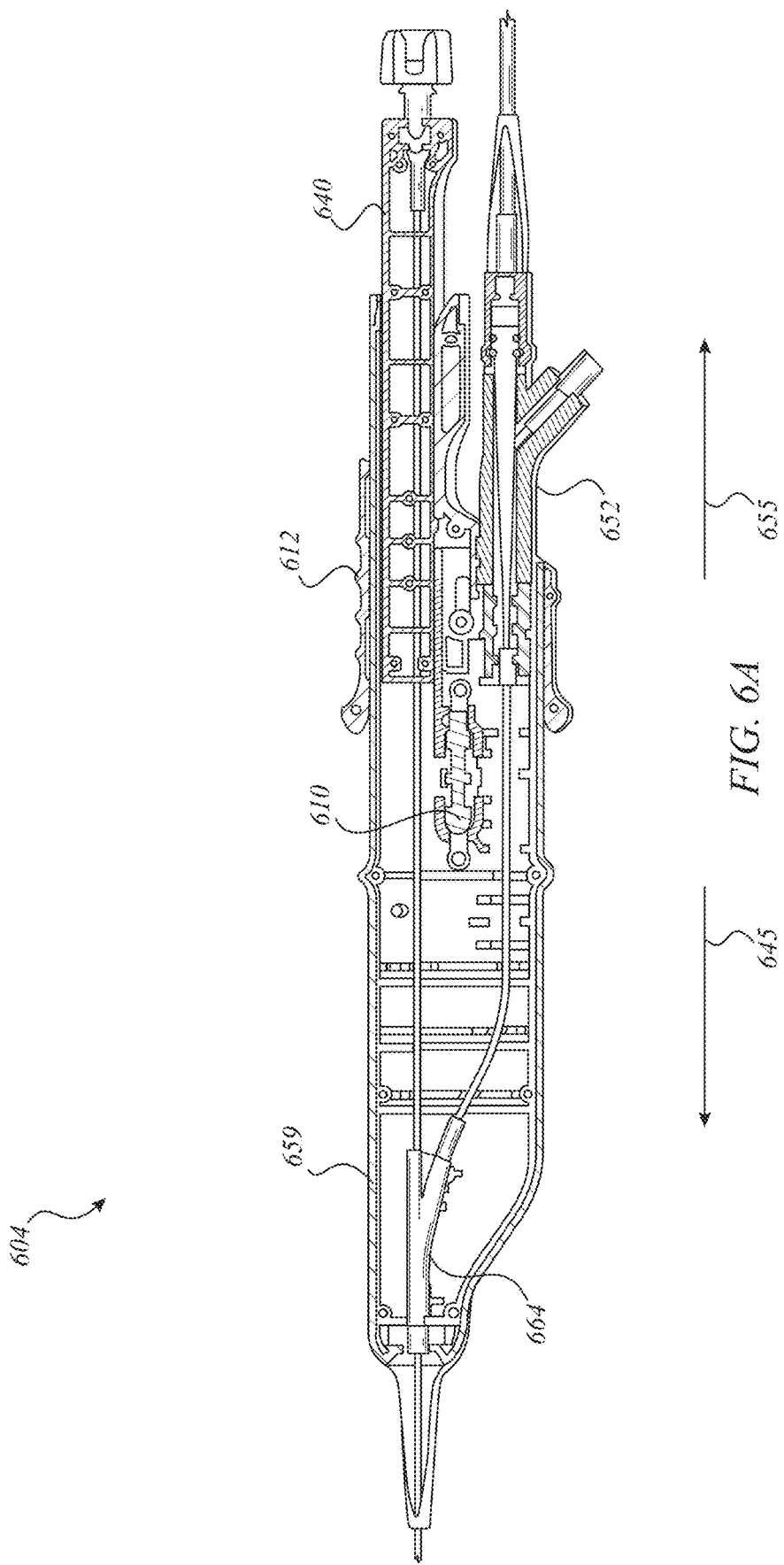
FIGS. 6A and 6B illustrate various internal components of an exemplary handle assembly according to one or more embodiments disclosed hereby.
Figure 6B:
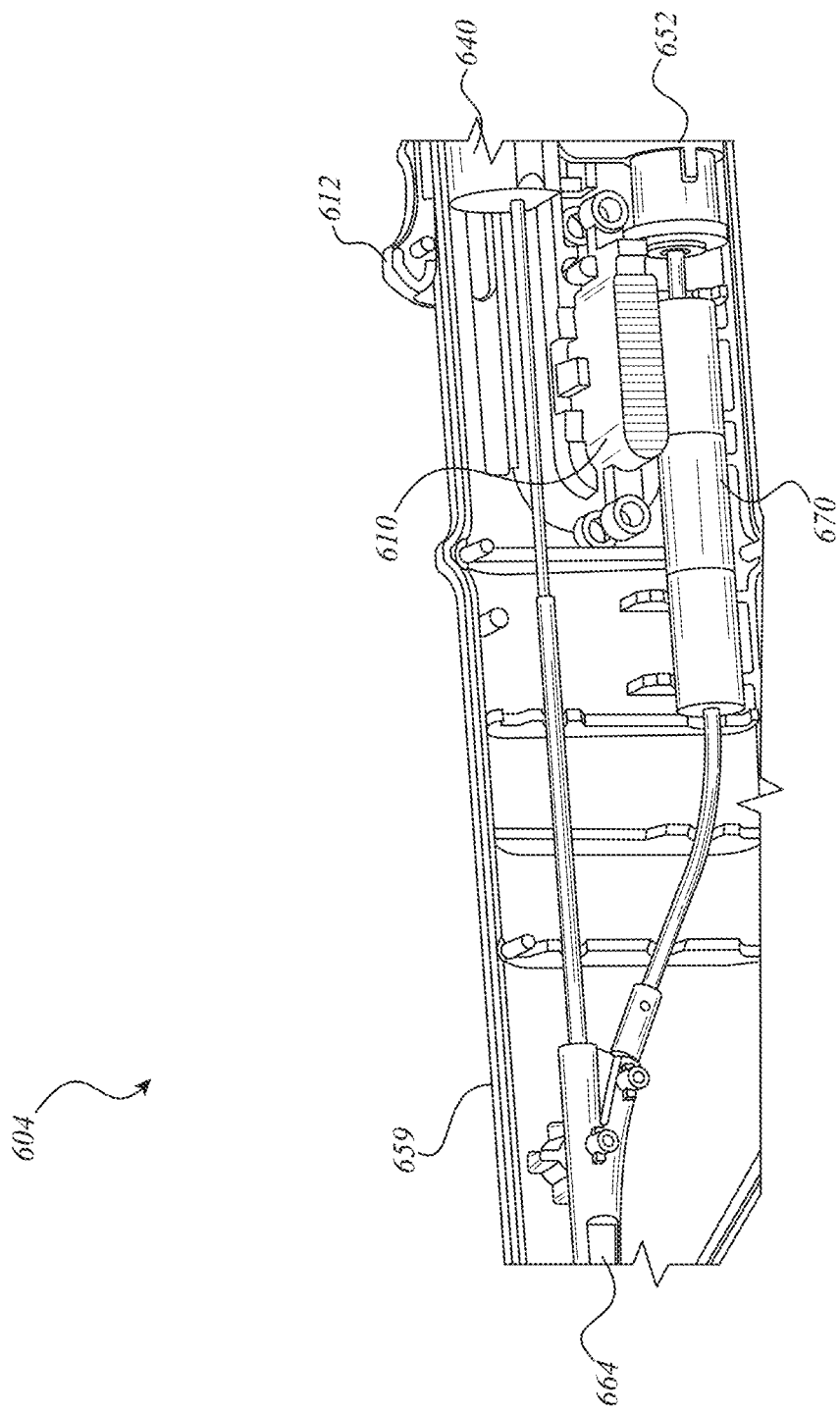

FIGS. 6A and 6B illustrate various internal components of an exemplary handle assembly 604 for a dual-function device according to one or more embodiments disclosed hereby. More specifically, FIG. 6A illustrates a first cross-sectional view of the handle assembly 604 having a distal end 645 and a proximal end 655, and FIG. 6B illustrates a second cross-sectional view of the handle assembly 604. In the illustrated embodiments, handle assembly 604 includes a handle body 659 comprising and/or coupling to a bifurcation joint 664, tool lock 610, actuation member 612, plunger assembly 640, flush port assembly 652, and noise compensators 670. In embodiments disclosed hereby, components of the handle assembly 604 may facilitate intuitive, ergonomic, and/or single-handed operations to target specific tissues in reliable, intuitive, unique, and advantageous ways. For example, handle assembly 504 may utilize intuitive motions for gripping, locking, unlocking, and actuating to provide for convenient, comfortable, accurate, and fatigue minimizing operation. In various embodiments, noise compensators 670 may serve to reduce electrical noise in the distal and/or proximal drive cables. For example, noise compensators 670 may be an electronic choke, such as a passive electric component that suppresses high frequency noise in electronic circuits. In some embodiments, one or more of noise compensators 670 may utilize ferrite, such as a ferrite ceramic. In many embodiments, one or more components illustrated in FIGS. 6A and 6B, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

Figure 7A:
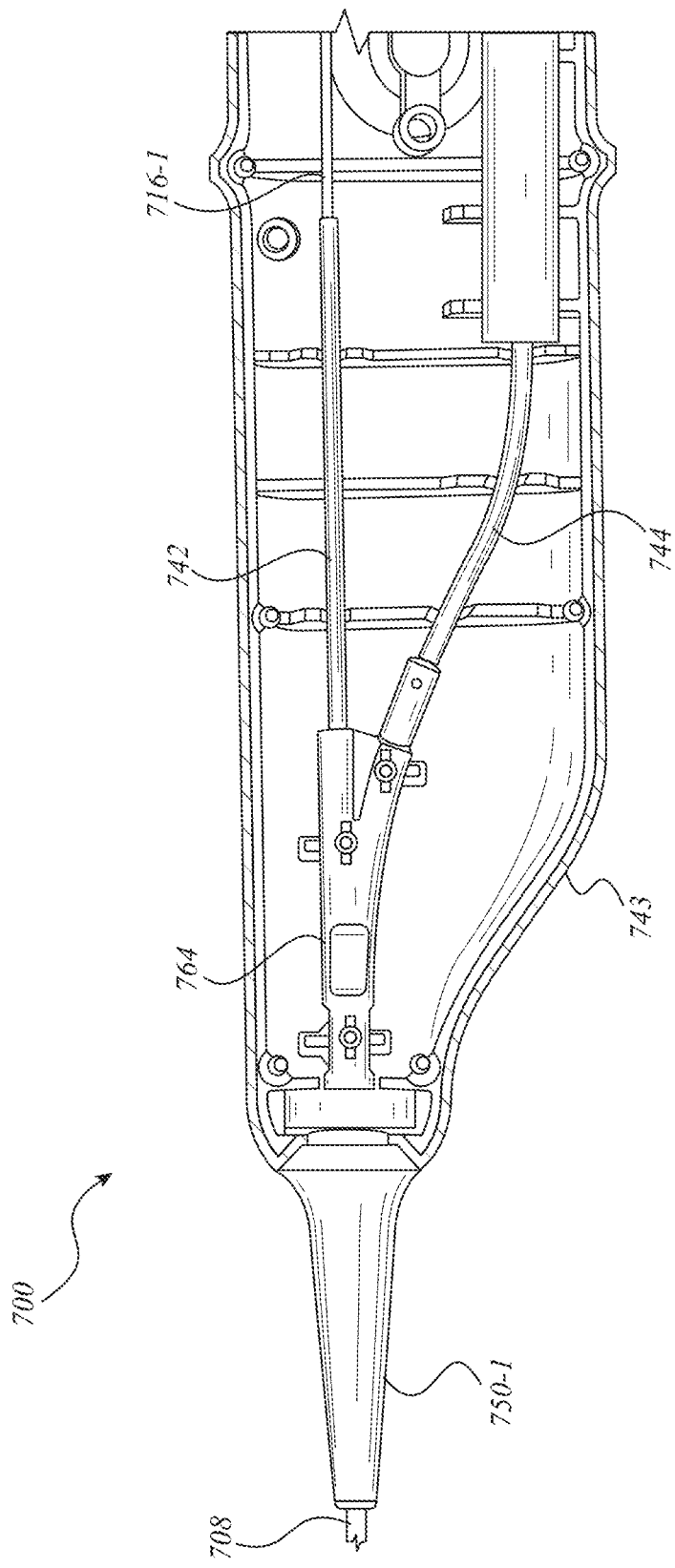
FIGS. 7A-7D illustrate various aspects of an exemplary bifurcation joint for a handle assembly according to one or more embodiments disclosed hereby.
Figure 7B:
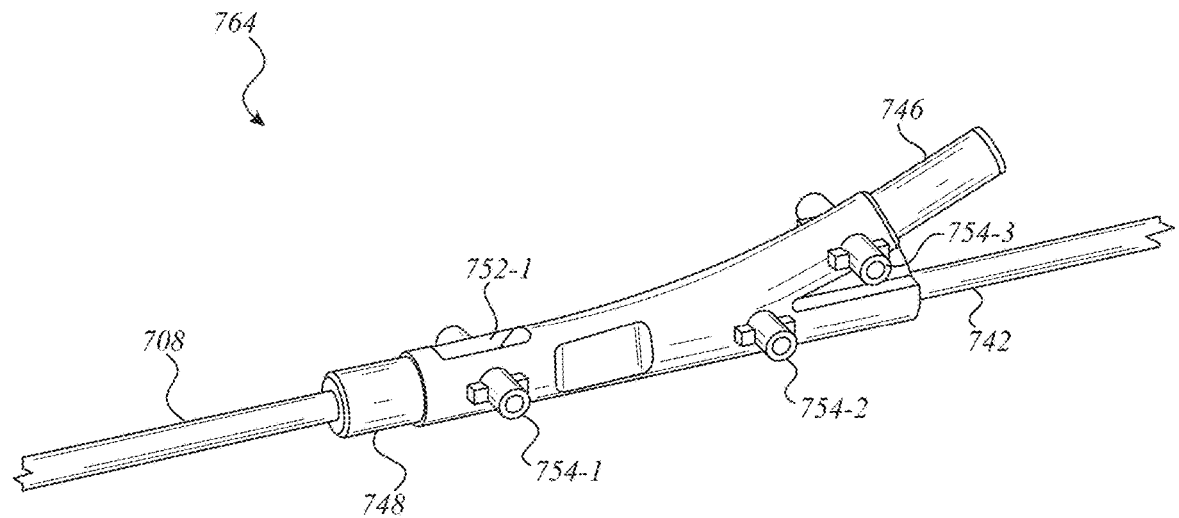
Figure 7C:
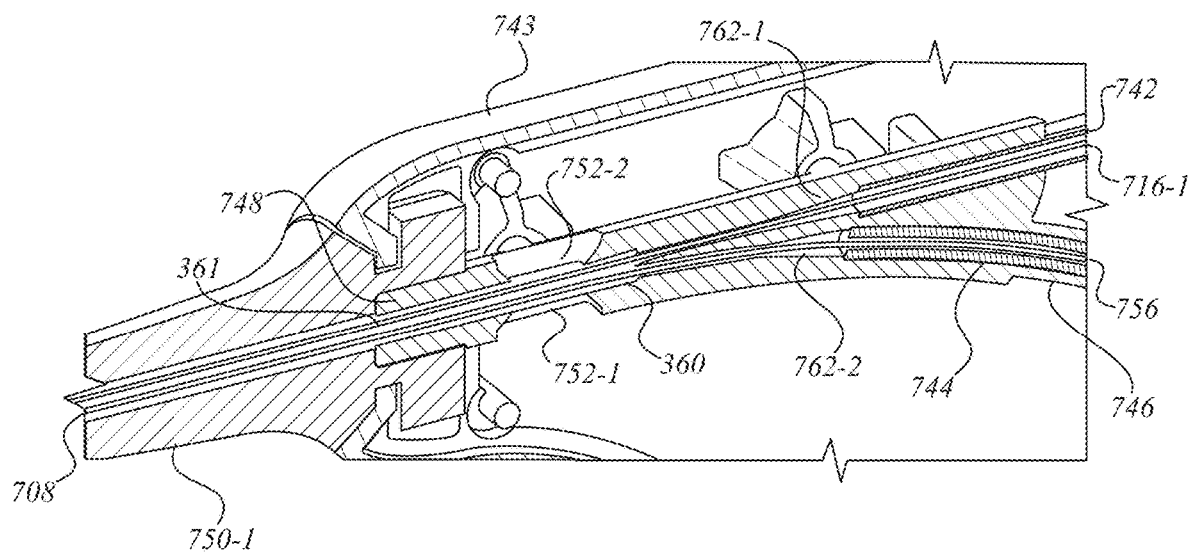
Figure 7D:
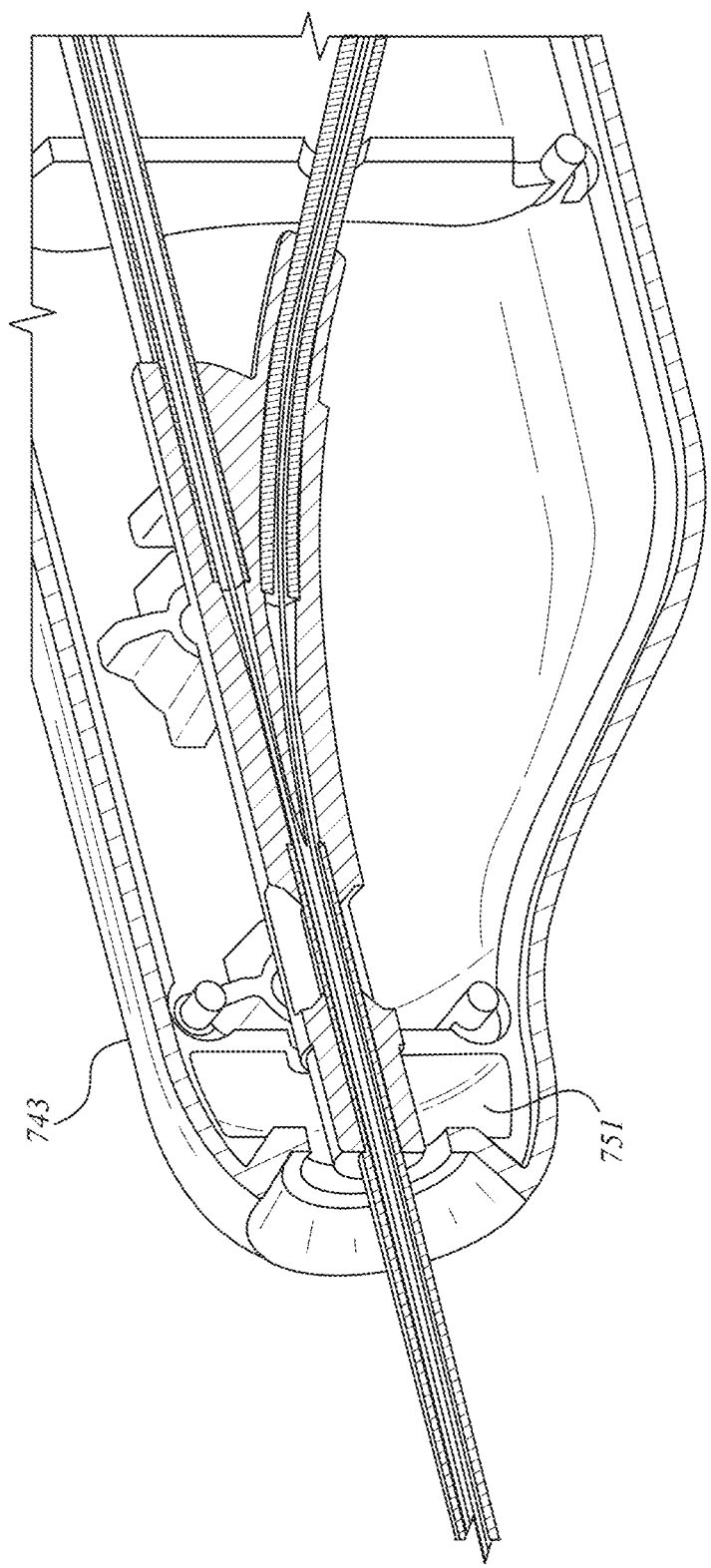

FIGS. 7A-7D illustrate various aspects of an exemplary bifurcation joint 764 for a dual-function device 700 according to one or more embodiments disclosed hereby. More specifically, FIG. 7A illustrates a cross-sectional view of the bifurcation joint 764 in conjunction with a handle body 743. FIG. 7B illustrates the bifurcation joint 764. FIGS. 7C and 7D illustrate cross-sectional views of bifurcation joint 764. In various embodiments, bifurcation joint 764 may connect the ablation tool 716-1 to a first lumen of dual-lumen catheter 708 and a conduit 744 carrying a portion of the distal drive cable 756 to a second lumen of dual-lumen catheter 708. In many embodiments, the bifurcation joint 764 may prevent fluid leaking within the handle body 743 when fluids are passed into the dual-lumen catheter. In embodiments disclosed hereby, components of the bifurcation joint 764 may facilitate convenient, reliable, efficient, and leak-proof operation in unique and advantageous ways. For example, the bifurcation joint 764 may reduce or minimize the bend in conduit 744 to limit bend in the drive cable (e.g., ultrasound drive cable). In another example, bifurcation joint 764 includes a tool support 742 to prevent ablation tool 716-1 from bending, such as when it is forced distally by the plunger assembly. In many embodiments, one or more components illustrated in FIGS. 7A-7D, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

Referring to FIG. 7A, bifurcation joint 764 may be disposed in handle body 743 and include tool support 742. More generally, bifurcation joint 764 may be the component of the dual-function device that routes the first and diagnostic tools into the first and second lumens of the dual-lumen catheter. In many embodiments, bifurcation joint 764 may align the first and diagnostic tools for insertion into the dual-lumen catheter 708 while limiting the amount of bend required. For instance, bifurcation joint 764 may prevent either tool from bending over 20 degrees. In another instance, bifurcation joint 764 may limit bending of a drive cable for a dual-function device to less than 15 degrees. In many embodiments, the minimum radius of curvature for the drive cable may be 3 inches.

Dual-function device 700 may also include strain relief 750-1. Strain relief 750-1, or one or more other strain reliefs disclosed hereby, may limit bending (e.g., bends over 25 degrees) of the dual-lumen catheter 708 or other portions along the length of tool lumens (e.g., conduit 744). In some embodiments, conduit 744 may comprise a polymer tube, such as a PEEK or Nylon tube. In several embodiments, bifurcation joint 764 supports parallel alignment of the plunger assembly and the flush port assembly in the handle assembly, resulting in an ergonomic and intuitive feel.

Referring to FIG. 7B, the dual-lumen catheter 708 may connect into the bifurcation join 764 at a catheter support 748, conduit 744 may connect into the bifurcation joint 764 at conduit support 746, and the ablation tool 716-1 may connect into tool support 742. In many embodiments, tool support 742 may prevent the ablation tool from kinking, paperclipping, bending, and/or breaking. Bifurcation joint 764 may also include mounts 754-1, 754-2, 754-3 (or mounts 754) on both sides and/or indentations 753-1, 753-2 (or indentations 753). In many embodiments, the mounts 754 may be used to attach the bifurcation joint 764 to handle body 743. As previously mentioned, in one or more embodiments, handle body 743 may connect one or more components of a dual-function device, such as by serving as one or more of a mounting point, enclosure, structure, and the like. Additionally, or alternatively, bifurcation joint 764 may include one or more view windows 752-1, 752-2 (or view windows 752). In various embodiments, the view windows 752 may allow visual verification the contents of the lumens as they pass through the bifurcation joint.

FIG. 7C includes a cross-sectional view of the bifurcation joint 764. As shown in FIG. 7C, the layer of braid 360 and the tubular member (not labeled) begin on the proximal side of the indentations 752 and the layer of reflow 361 on the dual-lumen catheter begins at the distal end of the bifurcation joint 764. Additionally, or alternatively, conduit 744 ends between the view windows 752 and the conduit support 746. The tool support 742 ends proximate to the end of conduit 744. In several embodiments, immediately distal of the tool support 742, the first lumen of the bifurcation joint includes a junction taper 762-1. In various embodiments, immediately distal of the conduit 744, the second lumen of bifurcation joint includes a junction taper 762-2. In some embodiments, the junction tapers 762 facilitate one or more of retaining the conduit/tool support connected, limiting a bending radius, and improving fluid flow (such as preventing leaks or reducing turbulent flow). In dual-function device 700, ablation tool 716-1 may pass through the first lumen of bifurcation joint 764 and distal drive cable 756 may pass through the second lumen of bifurcation joint 764. FIG. 7D illustrates handle body 743 with strain relief 750-1 removed, leaving strain relief pocket 751.

Figure 8A:
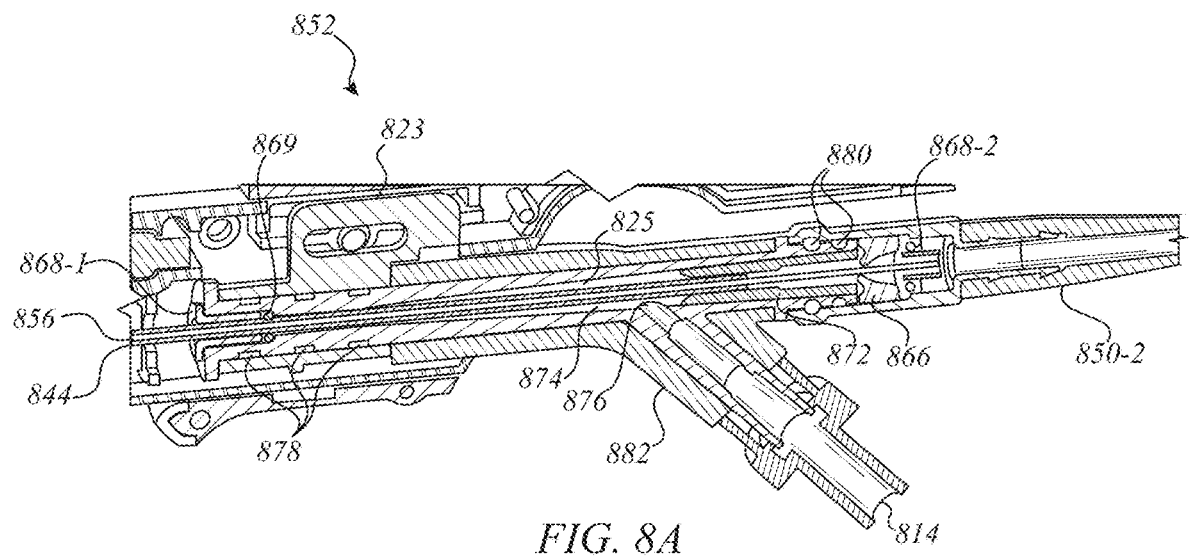
Figure 8B:
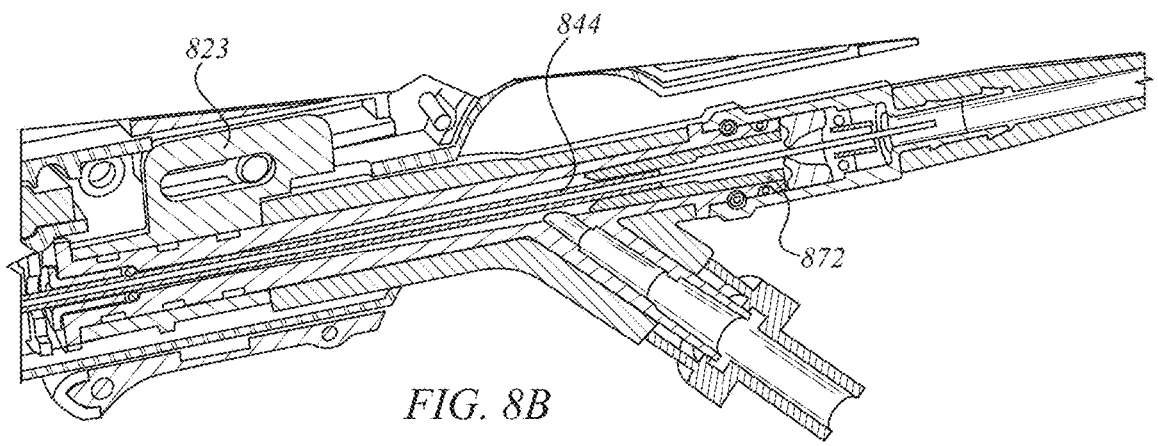
Figure 8C:
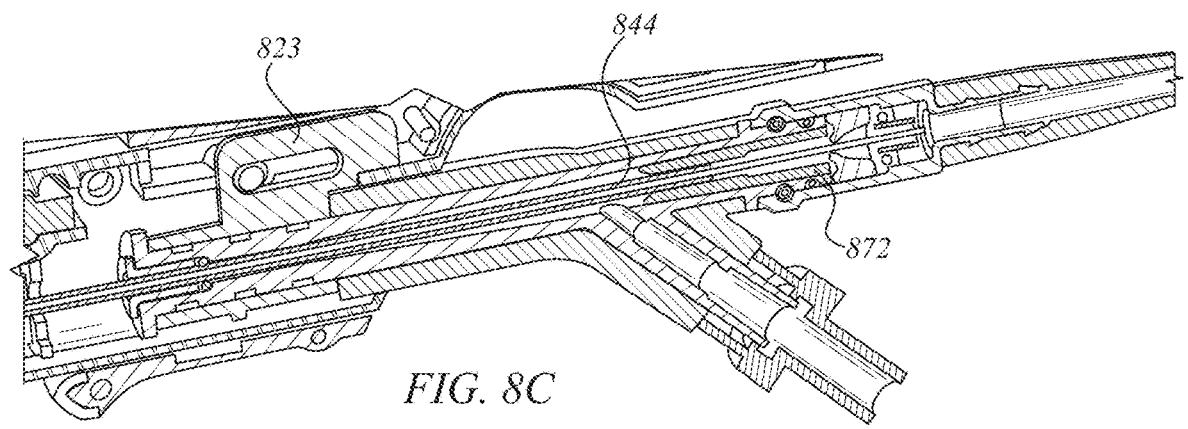
Figure 8D:
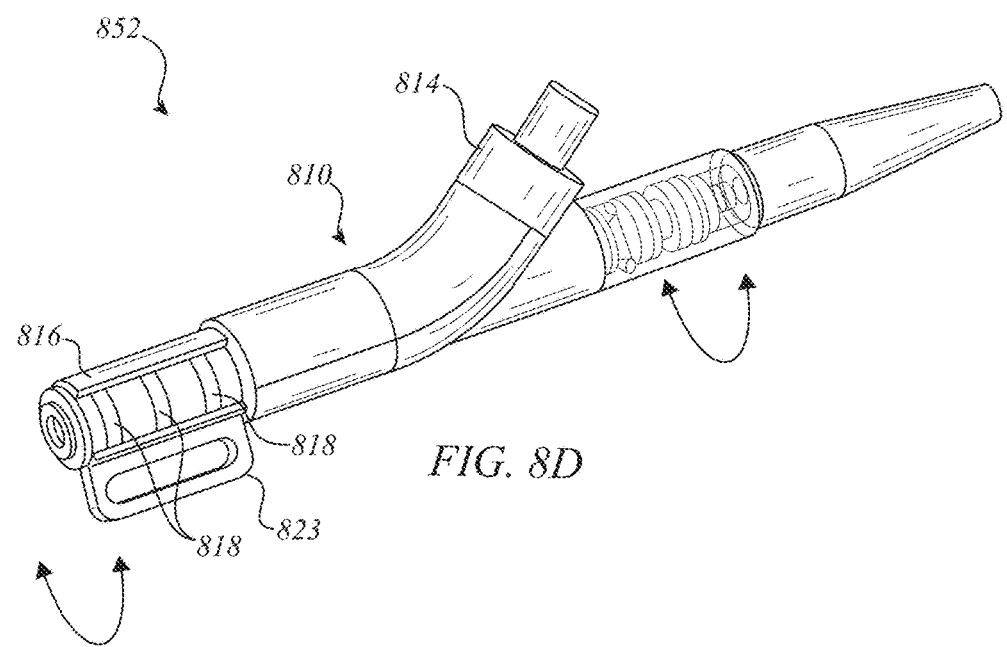
Figure 8E:
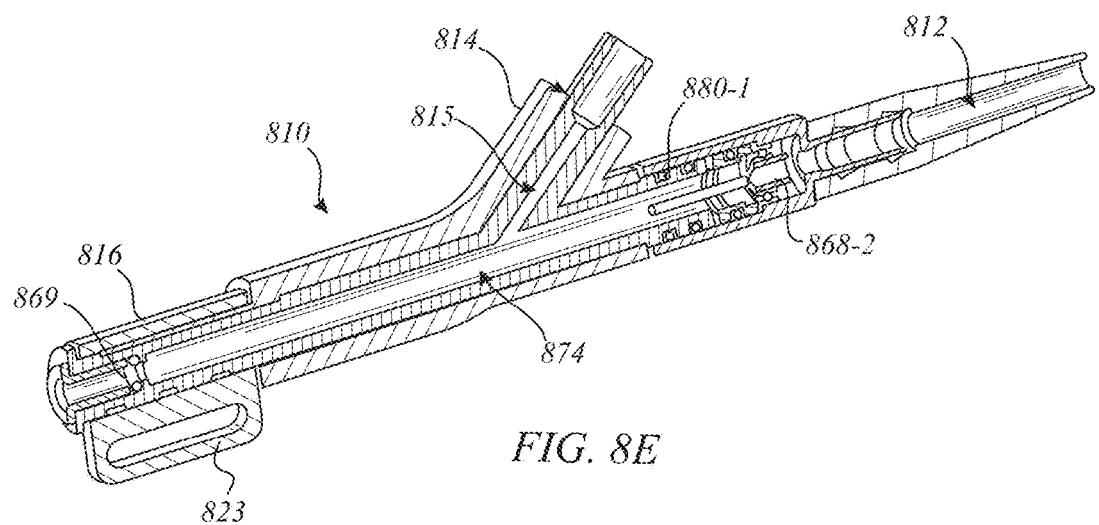
Figure 8F:
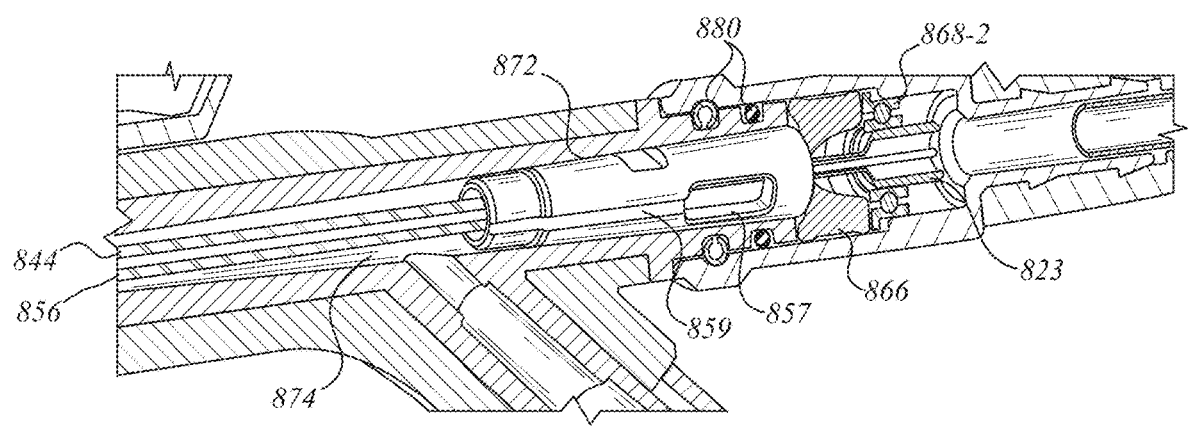
Figure 8I:
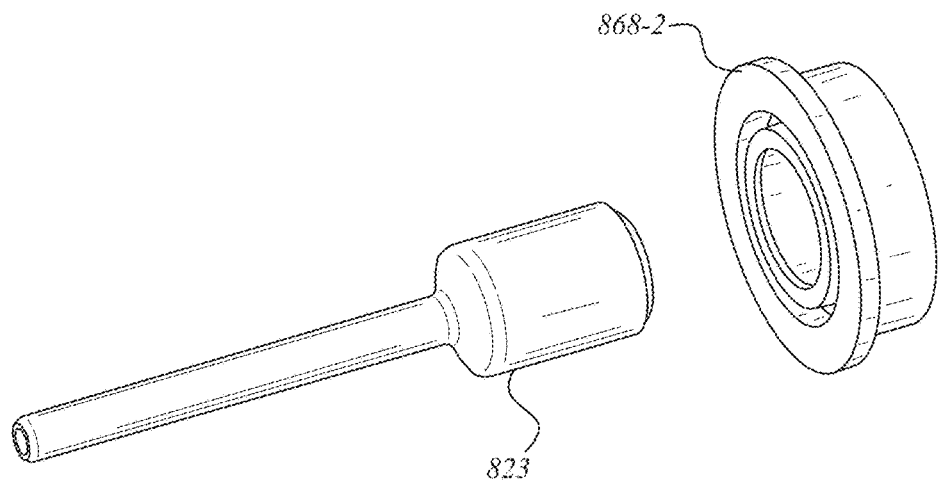
Figure 8J:
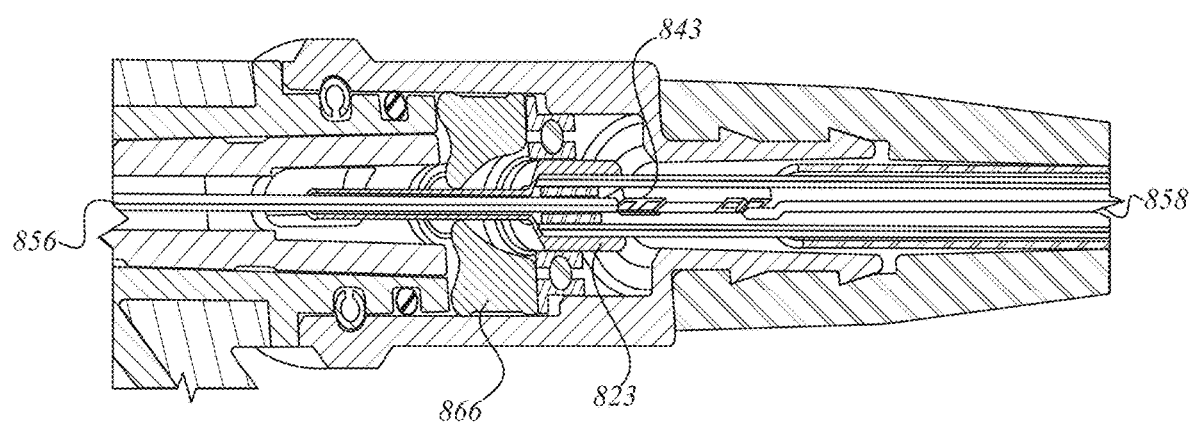

FIGS. 8A-8J illustrate various aspects of an exemplary flush port assembly 852 for a dual-function device according to one or more embodiments disclosed hereby. More specifically, FIG. 8A illustrates a cross-sectional view of the flush port assembly 852. FIGS. 8B and 8C illustrate axial displacement of flush port assembly 852 in distal and proximal directions, respectively. FIG. 8D illustrates axial rotation of flush port assembly 852. FIG. 8E illustrates various aspects of the flush port assembly 852. FIG. 8F illustrates various components of flush port assembly 852. FIG. 8G illustrates a flow path 861 from flush port 814 into conduit 844. FIGS. 8H and 8I illustrate various aspects of the flush port assembly 852 including a stabilizer 823 and a bearing 868-2. FIG. 8J illustrates an impedance compensator 843 disposed between a distal drive cable 856 and a proximal drive cable. In embodiments disclosed hereby, components of the flush port assembly 852 may facilitate convenient, reliable, efficient, and leak-proof operation in unique and advantageous ways. For example, the flush port assembly 852 may rotate independently of the proximal and distal drive cables 856, 858 while maintaining a seal with conduit 844 that facilitates introduction of fluid into the conduit 844 around the distal drive cable 856. In another example, impedance compensator 843 matches impedance between the distal and proximal drive cables 856, 858. In many embodiments, one or more components illustrated in FIGS. 8A-8J, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure.

Referring to FIG. 8A, flush port assembly 852 may include bearings 868-1, 868-2, seal 869, slide mount 823, proximal surface features 880, strain relief 850-2, lip seal 866, port member 872, flush port 814, port interface 882, flow junction 876, flow chamber 874 with taper 825, distal surface features 878, a proximal portion of conduit 844, a portion of the distal drive cable 856 and a portion of the proximal drive cable 858. One or more components disclosed hereby (e.g., port interface 882) may be formed via a molding, extrusion, and/or machining procedure (e.g., overmolding, injection molding, vacuum molding, cold extrusion, lathe, and the like).

As previously mentioned, the flush port assembly 852 may be able to be adjusted in the proximal and distal directions. Accordingly, FIG. 8B illustrates the port assembly 852 including slide mount 823, conduit 844, and port member 872 in the distal most position and FIG. 8C illustrates the port assembly 852 including slide mount 823, conduit 844, and port member 872 in the proximal most position. In many embodiments, conduit 844 may be supported by a slide within port member 872 as it is proximally and distally moved with respect to the longitudinal axis of the device. The slide mount 823 may couple with a peg or mounting point on the handle body. In various embodiments, adjustment along slide mount 823 may be utilized to calibrate the location of the imaging transducer with respect to the imaging window, such as during manufacture. In some embodiments, the end user may be able to adjust along the slide mount 823.

Referring to FIGS. 8D-8E, in one embodiment, a flush port assembly 852 of the present disclosure may include a housing 810 defining a flow chamber 874. An ultrasound port 812 (e.g., first port) may be formed within or otherwise extend through a proximal portion of the housing 810. In various embodiments, the ultrasound port 812 may be coextensive (e.g., substantially aligned with, etc.) with the flow chamber 874. A flush port 814 (e.g., second port) defining a fluid channel 115 therethrough may be disposed along (e.g., attached to, integrally formed with, etc.) a middle portion of the housing 810. A fitting 816 may be disposed around a distal portion of the housing 810. In various embodiments, the housing 810 may be configured to rotate 360° (e.g., move axially) within the fitting 816 to alter a position of the flush port 814 relative to a longitudinal axis of the flush port assembly 852 (e.g., move proximally or distally) and/or rotate (e.g., alter an axial position of) a radial ultrasound probe extending through the housing 810 (as discussed below). An outer surface of the distal portion of the housing may include distal surface features 818 configured to frictionally engage a corresponding inner surface of the fitting 816. By way of non-limiting example, the surface feature may include a rubber seal or O-ring configured to maintain or lock an axial position of the housing 810 relative to the fitting 816 until a threshold level of rotational force is exerted on the housing 810 (e.g., a sufficient amount of force exerted by a physician's hand). In various embodiments, an outer surface of the housing 810 and/or flush port 814 may include a non-slip surface (e.g., over-molded or coated with rubber, etc.) to provide a physician with sufficient grip to manipulate the housing 810, e.g., when wearing wet gloves, etc. Slide mount 823 (e.g., an arm or projection) may extend from an outer surface of the fitting 816 to anchor or lock the housing of the probe assembly within a handle body (e.g., handle body 743) of a dual-function device with radial ultrasound and ablation capability.

In one embodiment, a first seal 869 (e.g., O-ring, etc.) may be disposed within a distal portion of the flow chamber 874 (e.g., proximal to a distal opening of the housing 810) and a second seal 124 may be disposed within a proximal portion of the flow chamber 874 (e.g., distal to a proximal opening of the housing 810). The first and second seals 869, 880-1 may be configured to prevent fluid introduced (e.g., flushed) through the fluid channel 815 of the flush port 814 from exiting the flow chamber 874 (e.g., flowing/leaking distally beyond the first seal 869 or proximally beyond the second seal 124). A bearing 126 may be disposed within the proximal portion of the flow chamber 874 proximal to the second seal 124. In various embodiments, the housing 810 and ultrasound port 812 may be configured to receive a proximal portion of a tool (e.g., a radial ultrasound probe) therethrough. The bearing 126 may be configured to receive an outer surface of the radial ultrasound probe 130 to support/facilitate rotation of the radial ultrasound probe within the housing 810.

FIGS. 8F and 8G illustrate various components of the flush port assembly 852, such as those associated with fluid flow. The flush port assembly 852 of FIG. 8F includes conduit 844, port member 872, proximal surface features 880, bearing 868-2, stabilizer 823, lip seal 866, flow port 857, flow channel 859, flow chamber 874, distal drive cable 856, and conduit 844. FIG. 8G illustrates a flow path 861 of fluid introduced via the flush port 814. Accordingly, the flow path 861 may enter via the flush port 814, fill flow chamber 874, follow flow channel 859 of port member 842, enter flow port 857 of port member 872, and proceed into the conduit 844 around the distal drive cable 856. In various embodiments, the lumens and/or flow components disclosed hereby may be designed to handle at least 43 pounds per square inch. Such pressure rating may vary as dictated by design and/or performance requirements.

FIG. 8H illustrates stabilizer 823, lip seal 866, and bearing 868-2 and FIG. 8I illustrates stabilizer 823 and bearing 868-2. In various embodiments, the stabilizer 823 may extend through one or more of the bearing 868-2 and lip seal 866. The drive cable may extend through the stabilizer 823. In many embodiments, the stabilizer may prevent loss of stability during rotation of the drive cable.

Referring to FIG. 8J, proximal of the stabilizer 823, an impedance compensator 843 may connect distal drive cable 856 and proximal drive cable 858. In several embodiments, the proximal and distal drive cable along with the imaging transducer may rotate at up to 2000 or more revolutions per minute (rpm). For instance, the imaging transducer (and drive cables) may rotate at 1800 rpm. In various embodiments, impedance compensator 843 may adapt for a diameter change between the distal and proximal drive cables 856, 858. In many embodiments, the impedance compensator spins along with the distal and proximal drive cables 856, 858. In one or more embodiments, the impedance compensator 843 comprises a printed circuit board (PCB). In many embodiments, the lumen of the distal drive cable 856 is a uniform size to prevent kinking or winding up of the distal drive cable. In some embodiments, the diameter change between the proximal and distal drive cables prevents signal degradation. For example, if the proximal drive cable was as small as the distal drive cable, unacceptable levels of signal degradation may occur. In some embodiments, making the proximal drive cable 856 have a larger diameter than the distal drive cable 858, reduced electromagnetic emissions (e.g., noise) can be achieved, such as via lower signal voltages. In several embodiments, one or more of the stabilizer 823, and the impedance compensator 843 may be filled with epoxy, such as to prevent fluid from leaking around the distal drive cable 856 and into the impedance compensator 843 via the stabilizer 823.

FIG. 9 illustrates various internal components of an exemplary imaging controller 990 of a dual-function device 900 according to one or more embodiments disclosed hereby. Controller 990 may include logic circuitry 992, memory 994, input/output (I/O) 996, and user interface 998. As previously mentioned, imaging controller 990 may couple with an imaging transducer 916-2 via a proximal drive cable 958 connected between the hub assembly 906 and an impedance compensator 943, and a distal drive cable 956 connected between the impedance compensator 943 and the imaging transducer 916-2. In embodiments disclosed hereby, components of the imaging control 990 may facilitate intuitive, accessible, dynamic monitoring and control over imaging transducer 916-2 in reliable, valuable, unique, and advantageous ways. For example, imaging controller 990 may control one or more of the calibration, frequency, resolution, translation, interpretation, integration, analysis, and/or display of images generated by one or more dual-function devices disclosed hereby. In one or more embodiments, controller 990 may utilize one or more of historical, contextual, user input, and sensor data to control aspects of the dual-function device. For example, historical data may include sensor and/or imaging data from previous procedures. In some such embodiments, the historical data may be annotated based on user input. In many embodiments, one or more components illustrated in FIG. 9, or described with respect thereto, may be the same or similar in construction, function, and/or appearance as one or more other components disclosed hereby. Embodiments are not limited in this context, and one or more aspects and/or components may be incorporated into other embodiments disclosed hereby without departing from the scope of this disclosure, and one or more aspects and/or components may be incorporated into other embodiments disclosed hereby without departing from the scope of this disclosure.

In various embodiments, proximal and distal drive cable 958, 956 may comprise multiple conductors. In some embodiments, the drive cables may be coaxial cables. In various embodiment, the drive cables may provide one or more of power, torque, communication between the imaging transducer and the imaging controller. In many embodiments, the I/O 996 may comprise an electromagnetic wave generator (or wave generator). The wave generator may control one or more characteristics of the signal including power, waveform, and frequency modulation. For example, the wave generator may produce ultrasound frequencies for the diagnostic tool and radio frequencies for the therapeutic tool. In some embodiments, the wave generator may produce frequencies ranging from Very Low Frequency (VLF) to Infrared. In some embodiments, controller 990 may optimize the frequency, such based on user settings regarding target penetration depth.

In many embodiments, the frequency of the imaging transducer may be 30 Hz or more. More generally, lower frequencies can allow greater penetration depths into tissue, but at the cost of spatial resolution. For many ablation applications, a higher frequency, such as over 30 Hz may be utilized due to a target penetration depth of only a few millimeters. Further, the higher frequency would allow for high resolution of transmucosal layers, allowing ablation of tissue to be confirmed. In some embodiments, controller 990 may analyze the transmucosal layers to determine ablation depth (see e.g., FIG. 10).

In some embodiments, the I/O 996 may include a network interface. In some such embodiments, the controller may utilize the network interface to communication with disparate sources and/or consumers via one or more networks (see FIG. 12), such as the internet. For example, controller 990 may receive updates via the internet. In another example, controller 990 may enable remote viewing and/or operation of the dual-function device. In yet another example, controller 990 may communicate with one or more application programing interfaces (APIs) via the network interface. In yet another example, controller 990 may communicated data via the network interface for one or more of processing, analyzing, storage, and distribution. In yet another embodiment, controller 990 may setup and/or calibrate the diagnostic device and/or therapeutic device based on analysis of historical data in a remote data store.

One or more of the components, devices, and/or techniques disclosed hereby may be used as part of a system to facilitate the performance of medical procedures (e.g., peripheral nodule ablation) in a safe, efficient, and reliable manner. In many embodiments, the novel system may include one or more medical devices capable of locating a patient-specific anatomy, positioning a flexible elongate member for access to the patient-specific anatomy, and accessing the patient-specific anatomy in a safe, accurate, and reliable manner. In these and other ways, components/techniques described here may improve patient care, increase user experience, decrease learning curve, improve success rates, and/or decrease adverse outcomes via realization of a more efficient and better functioning medical device with advantageous features. In many embodiments, one or more of the advantageous features may result in several technical effects and advantages over conventional devices and technology, including increased capabilities and improved adaptability. In various embodiments, one or more of the aspects, techniques, and/or components disclosed hereby may be implemented in a practical application via one or more computing devices, and thereby provide additional and useful functionality to the one or more computing devices, resulting in more capable, better functioning, and improved computing devices. Further, one or more of the aspects, techniques, and/or components disclosed hereby may be utilized to improve one or more technical fields including imaging, endoscopy, cannulation, diagnosis, treatment, imaging, robotics, embedded systems and/or control systems.

In several embodiments, components disclosed hereby may provide specific and particular manners to render, interpret, transform, analyze, monitor, and/or characterize images generated by the dual-function device, such as via imaging transducer 316-2 (see e.g., FIG. 3B). In several such embodiments, the specific and particular manners may include, for instance, controlling, monitoring, and/or interfacing with one or more of a transducer, a joint, a working channel, and a user interface to facilitate one or more endoscopy procedures. In one example, the specific and particular manner may simplify pulmonary procedures to facilitate medical professional to quickly learn to safely and reliably ablate a target treatment site.

In many embodiments, one or more of the components disclosed hereby may be implemented as a set of rules that improve computer-related technology by allowing a function not previously performable by a computer that facilitates an improved technological result to be achieved. In many embodiments, the function allowed is associated with dual-function devices and/or procedures. For example, controller 990 may adjust the power level of ablation tool 947 based on data from ultrasound transducer 916-2. In some embodiments, controller 990 may automatically begin imaging when power to the ablation tool returns below a threshold. In some such embodiments, when power to the ablation tool is above the threshold, the ablation tool may generate too much noise for the imaging transducer to operate properly.

In various embodiments, the controller may utilize ultrasound transducer 916 to calibrate, train, and/or control one or more features of ablation tool 947. For example, controller 990 may determine tissue has been ablated to a specific depth and/or layer (see e.g., FIG. 10) and stop the ablation tool 947 based on data generated by the ultrasound transducer 916-2. In many embodiments, a controller may automate one or more processes disclosed hereby by implementing one or more control loops for the therapeutic device based on using data from the diagnostic device to adjust one or more settings and/or parameters of the therapeutic device.

In some embodiments, controller 990 may utilize historical data to configure the diagnostic and/or therapeutic device (e.g., set up or calibrate one or more of the diagnostic and therapeutic devices for a particular procedure based on historical data). In various embodiments, controller 990 may an ultrasound drive unit and an image processor. In many embodiments, controller 990 may include separate I/O ports for the diagnostic and therapeutic tools. One or more components or functionalities disclosed hereby may be included in a single housing, or in multiple housing or locations.

Figure 10:
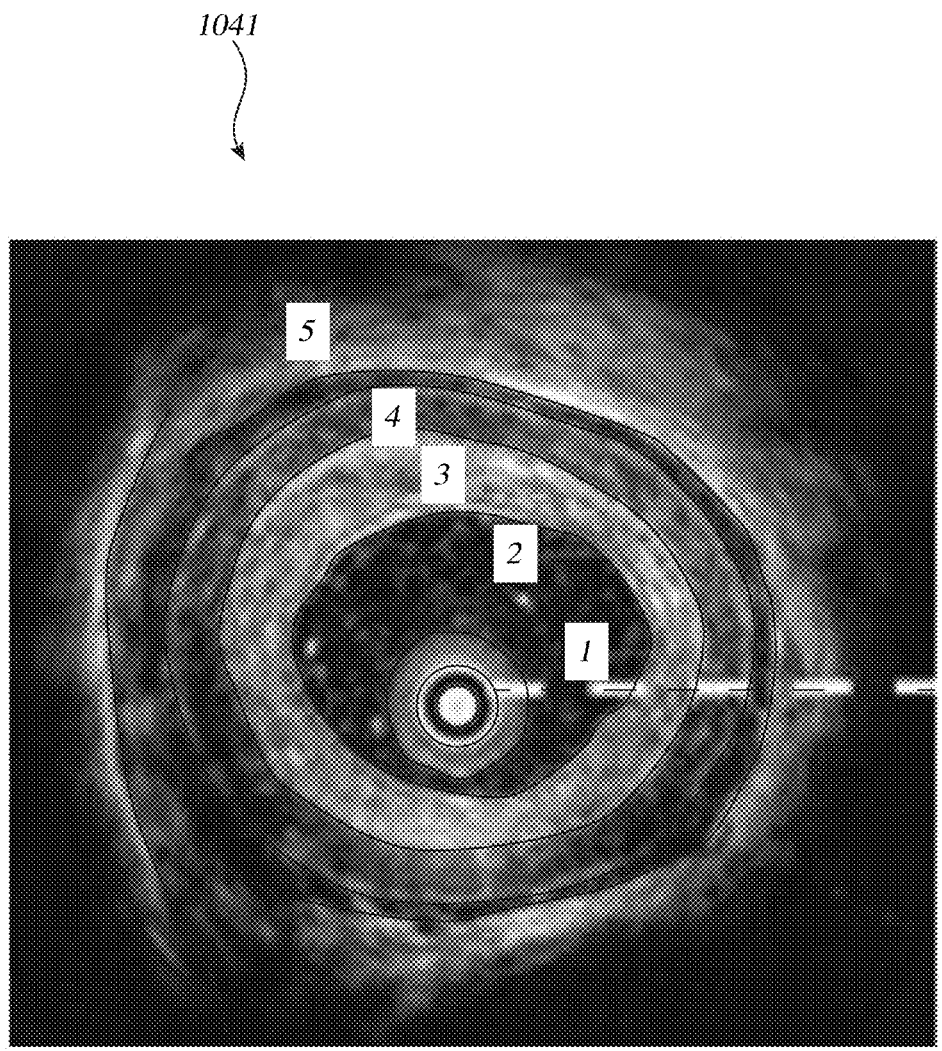
FIG. 10 illustrates various aspects of an exemplary ultrasound image according to one or more embodiments disclosed hereby.

FIG. 10 illustrates various aspects of an ultrasound image 1062 according to one or more embodiments disclosed hereby. Ultrasound image 1062 may include one or more layers or depths of tissue. In some embodiments, ultrasound image 1062 may comprise a composite image created by the controller. For example, ultrasound image 1062 may include a composite of images taken at different frequencies, perspectives, and/or locations. The illustrated embodiment of ultrasound image 1062 includes five layers of tissue. In several embodiments, the first layer may include an interface layer, the second layer may include a mucosa layer, the third layer may include a submucosa layer, the fourth layer may include a muscularis inner layer, and the fifth layer may include a muscularis outer layer. In many embodiments, controller 990 may analyze and identify the layers/depths/ablation of tissues based on ultrasound image 1062. Ultrasound image 1062 may be utilized, such as by controller 990, to determine when a target amount/depth of penetration has been achieved. For example, performance of an en bloc resection of a Grade IA or Grade IB bladder tumor may require removal of the submuscol layer, which can be confirmed by exposing the underlying smooth muscle layers. In another example, removal of a muscosal layer in the duodenum during a duodenal mucosal resurfacing. In some examples, removing of the muscosal layer in the duodenum may be utilized to alter an appetite of a patient and/or reduce diabetes factors, such as HbA1C %, In many embodiments, one or more components illustrated in FIG. 10, or described with respect thereto, may be the same or similar in construction, function, and/or appearance as one or more other components disclosed hereby. For example, ultrasound image 1062 may be the same or similar to ultrasound image 362. Embodiments are not limited in this context, and one or more aspects and/or components may be incorporated into other embodiments disclosed hereby without departing from the scope of this disclosure, and one or more aspects and/or components may be incorporated into other embodiments disclosed hereby without departing from the scope of this disclosure.

Figure 11:
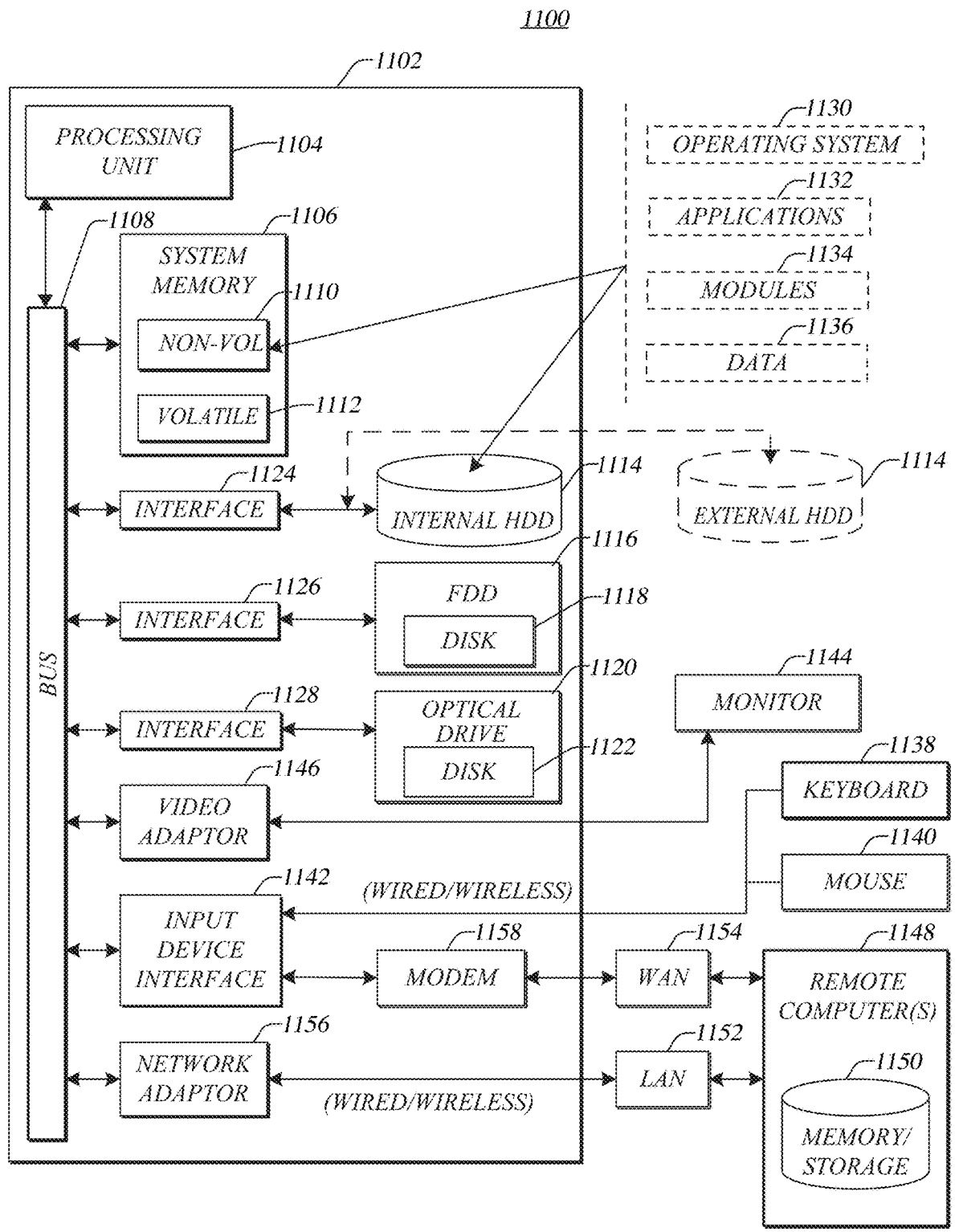
FIG. 11 illustrates an embodiment of a computing architecture according to one or more embodiments disclosed hereby.

FIG. 11 illustrates an embodiment of an exemplary computing architecture 1100 that may be suitable for implementing various embodiments as previously described. In various embodiments, the computing architecture 1100 may comprise or be implemented as part of an electronic device and/or medical device. In some embodiments, the computing architecture 1100 may be representative, for example, of one or more components disclosed hereby. In some embodiments, computing architecture 1100 may be representative, for example, of a computing device that implements or utilizes one or more portions of components and/or techniques disclosed hereby, such as controller 990, logic circuitry 992, memory, 994, I/O 996, and/or user interface 998. The Embodiments are not limited in this context, and one or more aspects and/or components may be incorporated into other embodiments disclosed hereby without departing from the scope of this disclosure.

As used in various embodiments herein, the terms "system" and "component" and "module" can refer to a computer-related entity, either hardware, a combination of hardware and software, software, or software in execution, examples of which are provided by the exemplary computing architecture 1100. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a controller 990 and the controller 990 can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1100 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1100.

As shown in FIG. 11, the computing architecture 1100 comprises a processing unit 1104, a system memory 1106 and a system bus 1108. The processing unit 1104 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1104.

The system bus 1108 provides an interface for system components including, but not limited to, the system memory 1106 to the processing unit 1104. The system bus 1108 can be any of several types of bus structure that may further interconnect to a memory bus (with or without a memory controller), a peripheral bus, and a local bus using any of a variety of commercially available bus architectures. Interface adapters may connect to the system bus 1108 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1106 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 11, the system memory 1106 can include non-volatile memory 1110 and/or volatile memory 1112. In some embodiments, system memory 1106 may include main memory. A basic input/output system (BIOS) can be stored in the non-volatile memory 1110.

The computer 1102 may include various types of computer-readable storage media in the form of one or more lower speed memory units, including an internal (or external) hard disk drive (HDD) 1114, a magnetic floppy disk drive (FDD) 1116 to read from or write to a removable magnetic disk 1118, and an optical disk drive 1120 to read from or write to a removable optical disk 1122 (e.g., a CD-ROM or DVD). The HDD 1114, FDD 1116 and optical disk drive 1120 can be connected to the system bus 1108 by an HDD interface 1124, an FDD interface 1126 and an optical drive interface 1128, respectively. The HDD interface 1124 for external drive implementations can include at least one or both of Universal Serial Bus (USB) and Institute of Electrical and Electronics Engineers (IEEE) 994 interface technologies. In various embodiments, these types of memory may not be included in main memory or system memory.

The drives and associated computer-readable media provide volatile and/or nonvolatile storage of data, data structures, computer-executable instructions, and so forth. For example, a number of program modules can be stored in the drives and memory units 1110, 1112, including an operating system 1130, one or more application programs 1132, other program modules 1134, and program data 1136. In one embodiment, the one or more application programs 1132, other program modules 1134, and program data 1136 can include or implement, for example, the various techniques, applications, and/or components disclosed hereby.

A user can enter commands and information into the computer 1102 through one or more wire/wireless input devices, for example, a keyboard 1138 and a pointing device, such as a mouse 1140. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1104 through an input device interface 1142 that is coupled to the system bus 1108 but can be connected by other interfaces such as a parallel port, IEEE 994 serial port, a game port, a USB port, an IR interface, and so forth.

A monitor 1144 or other type of display device is also connected to the system bus 1108 via an interface, such as a video adaptor 1146. The monitor 1144 may be internal or external to the computer 1102. In addition to the monitor 1144, a computer typically includes other peripheral output devices, such as speakers, printers, and so forth.

The computer 1102 may operate in a networked environment using logical connections via wire and/or wireless communications to one or more remote computers, such as a remote computer 1148. In various embodiments, one or more interactions disclosed hereby may occur via the networked environment. The remote computer 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wire/wireless connectivity to a local area network (LAN) 1152 and/or larger networks, for example, a wide area network (WAN) 1154. Such LAN and WAN networking environments are commonplace in offices and companies, and facilitate enterprise-wide computer networks, such as intranets, all of which may connect to a global communications network, for example, the Internet.

When used in a LAN networking environment, the computer 1102 is connected to the LAN 1152 through a wire and/or wireless communication network interface or adaptor 1156. The adaptor 1156 can facilitate wire and/or wireless communications to the LAN 1152, which may also include a wireless access point disposed thereon for communicating with the wireless functionality of the adaptor 1156.

When used in a WAN networking environment, the computer 1102 can include a modem 1158, or is connected to a communications server on the WAN 1154 or has other means for establishing communications over the WAN 1154, such as by way of the Internet. The modem 1158, which can be internal or external and a wire and/or wireless device, connects to the system bus 1108 via the input device interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Figure 12:
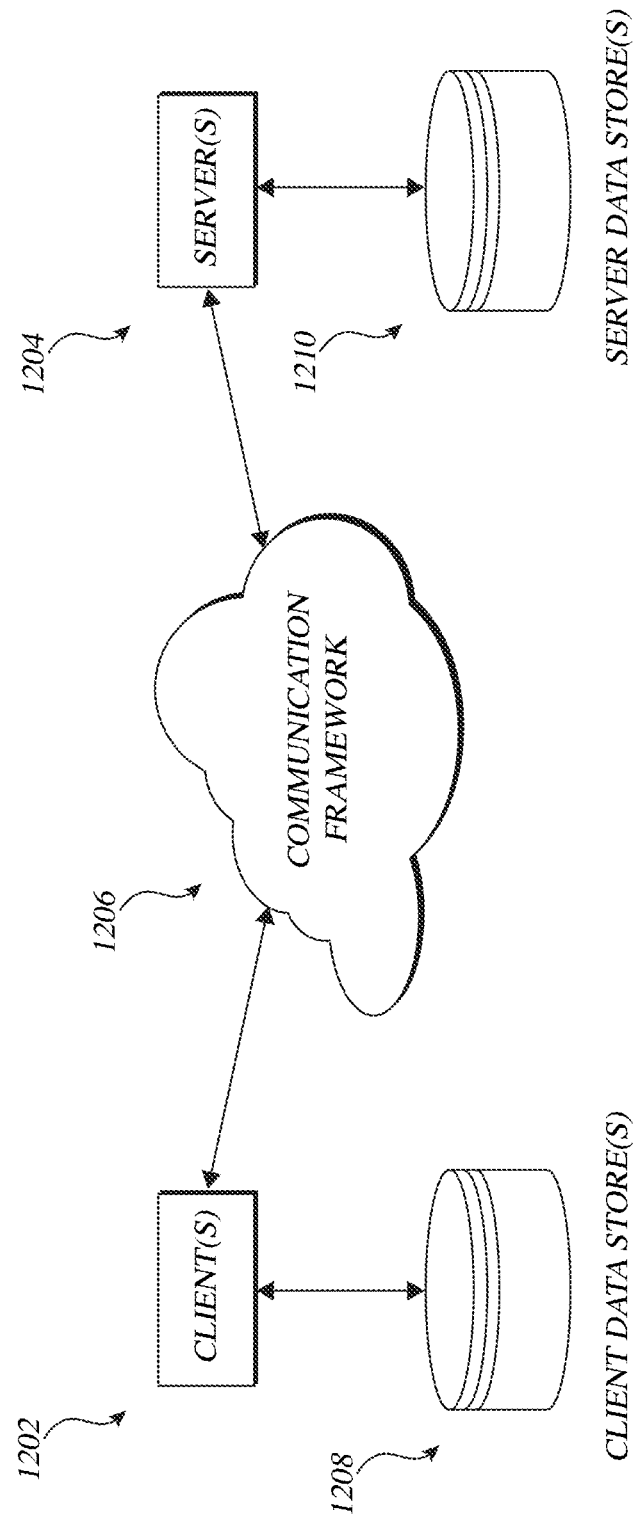
FIG. 12 illustrates exemplary aspects of a communications architecture according to one or more embodiments disclosed hereby.

FIG. 12 illustrates a block diagram of an exemplary communications architecture 1200 suitable for implementing various embodiments as previously described, such as applications or services disclosed hereby. The communications architecture 1200 includes various common communications elements, such as a transmitter, receiver, transceiver, radio, network interface, baseband processor, antenna, amplifiers, filters, power supplies, and so forth. The embodiments, however, are not limited to implementation by the communications architecture 1200.

As shown in FIG. 12, the communications architecture 1200 comprises includes one or more clients 1202 and servers 1204. The clients 1202 and the servers 1204 are operatively connected to one or more respective client data stores 1208 and server data stores 1210 that can be employed to store information local to the respective clients 1202 and servers 1204, such as cookies and/or associated contextual information. In various embodiments, any one of servers 1204 may implement one or more of logic flows, components, functionalities, or operations disclosed hereby, and storage mediums disclosed hereby, such as in conjunction with storage of data received from any one of clients 1202 on any of server data stores 1210.

The clients 1202 and the servers 1204 may communicate information between each other using a communication framework 1206. The communications framework 1206 may implement any well-known communications techniques and protocols. The communications framework 1206 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 1206 may implement various network interfaces arranged to accept, communicate, and connect to a communications network. A network interface may be regarded as a specialized form of an input output interface. Network interfaces may employ connection protocols including without limitation direct connect, Ethernet (e.g., thick, thin, twisted pair 10/100/1900 Base T, and the like), token ring, wireless network interfaces, cellular network interfaces, IEEE 802.11a-x network interfaces, IEEE 802.16 network interfaces, IEEE 802.20 network interfaces, and the like. Further, multiple network interfaces may be used to engage with various communications network types. For example, multiple network interfaces may be employed to allow for the communication over broadcast, multicast, and unicast networks. Should processing requirements dictate a greater amount speed and capacity, distributed network controller architectures may similarly be employed to pool, load balance, and otherwise increase the communicative bandwidth required by clients 702 and the servers 704. A communications network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor (e.g., logic circuitry), which when read by a machine causes the machine to fabricate logic to perform the techniques disclosed hereby. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine (e.g., logic circuitry), may cause the machine to perform a method and/or operation in accordance with the embodiments. Such a machine may include, for example, any suitable processing platform, computing platform, computing device, processing device, computing system, processing system, computer, processor, logic circuitry, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

This application relates to, and incorporates by reference in its entirety for all purposes, U.S. patent application Ser. No. 16/875,395, titled "Medical imaging devices, systems, and methods", filed on May 15, 2020, the entirety of which is incorporated herein by reference.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method disclosed hereby without departing from the concept, spirit and scope of the disclosure. All such similar substitutes and modifications apparent to those skilled in the art are deemed to be within the spirit, scope and concept of the disclosure as defined by the appended claims.

What is claimed is:

1. An apparatus, comprising:
    a handle assembly comprising a bifurcation joint, flush port assembly, and a device port configured to receive a therapeutic tool;
    an elongate member comprising a first lumen and a second lumen, wherein the bifurcation joint connects the flush port assembly to a proximal end of the first lumen and the device port to a proximal end of the second lumen; and
    a diagnostic tool extending though the flush port assembly, through the bifurcation joint, and into the first lumen,
    wherein the flush port assembly is configured to rotate, at least partially, about a longitudinal axis of the diagnostic tool.

2. The apparatus of claim 1, comprising the therapeutic tool, wherein the therapeutic tool extends through the device port, through the bifurcation joint, and into the second lumen.

3. The apparatus of claim 1, comprising a probe with a first opening and a second opening, wherein the probe connects a distal end of the first lumen to the first opening and a distal end of the second lumen to the second opening.

4. The apparatus of claim 3, wherein the first opening is orthogonal to the second opening.

5. The apparatus of claim 3, the probe comprising a ramped surface adjacent to the second opening, wherein the ramped surface is configured to deflect the therapeutic tool away from a longitudinal axis of the elongate member when the therapeutic tool is extended out of the second opening.

6. The apparatus of claim 1, comprising a plunger assembly configured to move the therapeutic tool in a distal and a proximal direction.

7. The apparatus of claim 6, comprising the therapeutic tool, wherein the therapeutic tool extends through the device port, through the plunger assembly, through the bifurcation joint, and into the second lumen.

8. The apparatus of claim 1, the diagnostic tool comprising an ultrasound transducer.

9. The apparatus of claim 8, wherein the ultrasound transducer operates at a frequency of more than 30 megahertz.

10. The apparatus of claim 1, the therapeutic tool comprising an ablation tool.

11. The apparatus of claim 10, the ablation tool comprising one or more of a ball-tipped laser fiber and a blunt-ended radio frequency ablation tool.

* * * * *